US011273204B2

(12) United States Patent
Gey et al.

(10) Patent No.: US 11,273,204 B2
(45) Date of Patent: Mar. 15, 2022

(54) IL-15 AND IL-15RAPLHA SUSHI DOMAIN BASED IMMUNOCYTOKINES

(71) Applicants: Cytune Pharma, Nantes (FR); UNIVERSITE PARIS DESCARTES, Paris (FR); ASSISTANCE PUBLIQUE-HOPITAUX DE PARIS, Paris (FR)

(72) Inventors: Alain Gey, Paris (FR); Eric Tartour, Paris (FR); David Bechard, Saint-Etienne de Montlu (FR)

(73) Assignees: CYTUNE PHARMA, Nantes (FR); UNIVERSITE DE PARIS, Paris (FR); ASSISTANCE PUBLIQUE—HOPITAUX DE PARIS, Paris (FR); INSTITUT NATIONAL DE LA SANTÉ ET DE LA RECHERCHE MÉDICALE (INSERM), Paris (FR)

( * ) Notice: Subject to any disclaimer, the term of this patent is extended or adjusted under 35 U.S.C. 154(b) by 0 days.

(21) Appl. No.: 14/910,475

(22) PCT Filed: Aug. 8, 2014

(86) PCT No.: PCT/EP2014/002181
§ 371 (c)(1),
(2) Date: Feb. 5, 2016

(87) PCT Pub. No.: WO2015/018528
PCT Pub. Date: Feb. 12, 2015

(65) Prior Publication Data
US 2016/0175459 A1 Jun. 23, 2016

(30) Foreign Application Priority Data
Aug. 8, 2013 (EP) .................................... 13003963

(51) Int. Cl.
| | | |
|---|---|---|
| *A61K 38/20* | (2006.01) | |
| *A61K 39/395* | (2006.01) | |
| *C07K 14/54* | (2006.01) | |
| *C07K 16/28* | (2006.01) | |
| *C07K 14/715* | (2006.01) | |
| *A61K 47/68* | (2017.01) | |
| *A61K 39/00* | (2006.01) | |

(52) U.S. Cl.
CPC ...... *A61K 38/2086* (2013.01); *A61K 47/6813* (2017.08); *A61K 47/6849* (2017.08); *C07K 14/5443* (2013.01); *C07K 14/7155* (2013.01); *C07K 16/2818* (2013.01); *A61K 2039/505* (2013.01); *C07K 2317/76* (2013.01); *C07K 2319/00* (2013.01); *Y02A 50/30* (2018.01)

(58) Field of Classification Search
CPC ............ A61K 47/6849; C07K 14/5443; C07K 2319/00
See application file for complete search history.

(56) References Cited

U.S. PATENT DOCUMENTS

| | | |
|---|---|---|
| 9,580,504 B1 | 2/2017 | Rotem-Yehudar et al. |
| 2012/0177595 A1 | 7/2012 | Wong et al. |
| 2015/0359853 A1* | 12/2015 | Felber ................... A61P 31/18 424/85.2 |
| 2016/0068584 A1 | 3/2016 | Bechard et al. |
| 2018/0312560 A1 | 11/2018 | Morisseau et al. |

FOREIGN PATENT DOCUMENTS

| | | |
|---|---|---|
| WO | 2007046006 A2 | 4/2007 |
| WO | 2008143794 A1 | 11/2008 |
| WO | 2009002562 A2 | 12/2008 |
| WO | 2011020047 A1 | 2/2011 |
| WO | 2012040323 A2 | 3/2012 |
| WO | 2012/175222 | 12/2012 |
| WO | 2012175222 A1 | 12/2012 |
| WO | 2015109124 A2 | 7/2015 |

OTHER PUBLICATIONS

Kermer et al. An antibody fusion protein for cancer immunotherapy mimicking IL-15 trans-presentation at the tumor site. Mol Cancer Ther. Jun. 2012;11(6):1279-88. Epub Apr. 6, 2012.*
Kontermann RE. Antibody-cytokine fusion proteins. Arch Biochem Biophys. Oct. 15, 2012;526(2):194-205. Epub Mar. 16, 2012.*
Yu et al. Simultaneous blockade of multiple immune system inhibitory checkpoints enhances antitumor activity mediated by interleukin-15 in a murine metastatic colon carcinoma model. Clin Cancer Res. Dec. 15, 2010;16(24):6019-28.*
Clinical Trial NCT01295827 Study of Pembrolizumab (MK-3475) in Participants With Progressive Locally Advanced or Metastatic Carcinoma, Melanoma, or Non-small Cell Lung Carcinoma. (Feb. 15, 2011).*
Steel et al., "Interleukin-15 1-16 biology and its therapeutic implications in cancer", Trends in Pharmacological Sciences, vol. 33, No. 1, Jan. 2012, pp. 35-41.
W. E. Carson, "Braking Bad: Blockade of Inhibitory Pathways Improves Interleukin-15 Therapy", Clinical Cancer Research, vol. 16, No. 24, Oct. 29, 2010, pp. 5917-5919.
International Search Report and Written Opinion for International Application No. PCT/EP2014/002181, dated Nov. 6, 2014.

(Continued)

*Primary Examiner* — Dong Jiang
(74) *Attorney, Agent, or Firm* — Kagan Binder, PLLC

(57) ABSTRACT

The present invention relates to an immunocytokine comprising (a) a conjugate, and (b) an immunomodulatory antibody or a fragment thereof directly or indirectly linked by covalence to said conjugate, wherein said conjugate comprises (i) a polypeptide comprising the amino acid sequence of the interleukin 15 or derivatives thereof, and a polypeptide comprising the amino acid sequence of the sushi domain of the IL-15Rα or derivatives thereof; and uses thereof.

7 Claims, 2 Drawing Sheets
Specification includes a Sequence Listing.

(56) References Cited

OTHER PUBLICATIONS

Stone et al., "Design and characterization of a protein superagonist of IL-15 fused with IL-15Rα and a high-affinity T cell receptor", Biotechnol Prog., 28(6), Nov. 2012, pp. 1588-1597.
Notice of Refusal for Japanese Application No. 2016-508046, dated Jan. 23, 2018, 8 pages.
Bessard et al., "High antitumor activity of RLI, an interleukin-I5 (IL-15)-IL-15 receptor a fusion protein, in metastatic melanoma and colorectal cancer", Molecular Cancer Therapeutics 8(9), Sep. 2009, pp. 2736-2745.
Janas et al. (2005) "Rituxan (anti-CD20 antibody)—induced translocation of CD20 into lipid rafts is crucial for calcium influx and apoptosis", Clinical and Experimental Immunology, 139:439-446.
Han et al. (2011) "IL-15:IL-15 receptor alpha superagonist complex: High-level coexpression in recombinant mammalian cells, purification and characterization", Cytokin—NIH Public Access Author Manuscript, 18 pages.
Kermer et al. (2014) "Combining Antibody-Directed Presentation of IL-15 and 4-1 BBL in a Trifunctional Fusion Protein for Cancer Immunotherapy", Molecular Cancer Therapeutics, 13(1):112-121.
Yu et al. (2010) "Simultaneous Blockade of Multiple Immune System Inhibitory Checkpoints Enhances Antitumor Activity Mediated by Interleukin-15 in a Murine Metastatic Colon Carcinoma Model", Clinical Cancer Research, 16(24):6019-6028.
Vincent et al. (2013) "Tumor targeting of the IL-15 superagonist RLI by an anti-GD2 antibody strongly enhances its antitumor potency", International Journal of Cancer, 133:757-765.
Vincent et al. (2011) "Development of two IL15 immunocytokines targeting either GD2- or CD20—tumoral bearing cells", Cytokinem 56, p. 102 (Abstract).
Xu et al. (2013) "Efficacy and Mechanism-of-Action of a Novel Superagonist Interieukin-15: Interleukin-15 Receptor aSu/Fc Fusion Complex in Syngeneic Murine Models of Multiple Myeloma", Cancer Research, 73(10):3075-3086 (Supplementary Material, pp. 1-4).
Xu et al. (2012) "The tumor immunosuppressive microenvironment impairs the therapy of anti-HER2/neu antibody", Protien Cells, 3(6):441-449.
Bessard et al. (2009) "High antitumor activity of RU, an interleukin-15 (II-15)-IL-15 receptor a fusion protein, in metastatic melanoma and colorectal cancer", Molecular Cancer Therapeutics, 8(9):2736-2745.
Kermer et al. (2012) "An Antibody Fusion Protein for Cancer Immunotherapy Mimicking IL-15 trans-Presentation at the Tumor Site" Molecular Cancer Therapeutics, 11(6):1279-1288.
Yu et al. (2012) "Simultaneous inhibition of two regulatory T-cell subsets enhanced Interleukin-15 efficacy in a prostate tumor model", PNAS, 109(16):6187-6192.
Mortier et al (2006) "Soluble Interleukin-15 Receptor a (IL-1 SRa)—sushi as a Selective and Potent Agonist of IL-15 Action through IL-15R beta/gamma", The Journal of Biological Chemistry, 281(3):1612-1619.
"PubChem Record Pidilizumab", SID 223366026—PubChem, IUPHAR/BPS Guide to Pharmacology, Nov. 13, 2014, 6 pages.

"Pidilizumab Report", IUPHAR/BPS Guide Io Pharmacology, Mar. 26, 2020, 2 pages.
"SEC submission from Medivation", U.S. Securities and Exchange Commission, Form 8-K, Medivation, Inc., Jan. 25, 2016, 4 pages.
Stenner et al. (2018) "Cancer Immunotherapy and the Immune Response in Follicular Lymphoma", Frontiers in Oncology, 8(219):1-7.
Vonderhelde et al. (2013) "Agonistic CD40 antibodies and cancer therapy", Clin. Cancer Res., 19(5):1035-1043.
Drew M. Pardoll (2012) "The blockade of immune checkpoints in cancer immunotherapy", Nature, 12:252-264.
Capece et al. (2012) "Targeting Costimulatory Molecules to Improve Antitumor Immunity", Journal of Biomedicine and Biotechnology, pp. 1-17.
Hamid et al. (2013) "Safety and Tumor Responseswith Lambrolizumab (Anti-PD-1) in Melanoma", The New England Journal of Medicine, 369(2):134-144.
EPO Letter Accompanying Subsequently Filed Items for European Application No. 14761280.8, dated Dec. 22, 2021, (83 pages).
Peggs et al., "Cancer immunotherapy: co-stimulatory agonists and co-inhibitory antagonists," Clinical and Experimental Immunology, vol. 157, pp. 9-19, 2009, (11 pages).
Medivation Press Release, 'U.S. FDA Lifts Partial Clinical Hold On Medivation's Pidilizumab', Mar. 9, 2016, retrieved from 'https://www.sec.gov/Archives/edgar/data/1011835/000119312516497500/d155319dex991.htm,' (2 pages).
Brocks et al., "Species-Crossreactive scFv Against the Tumor Stroma Marker "Fibroblast Activation Protein" Selected by Phage Display From an Immunized FAP−/− Knock-Out Mouse," Molecular Medicine, vol. 7, No. 7, pp. 461-469, 2001, (9 pages).
"Lenalidomide and Pidilizumab in Treating Patients With Relapsed or Refractory Multiple Myeloma," Trial record 1 of 1 for: NCT02077959, First Posted Mar. 4, 2014, Last Update Posted May 30, 2019, retrieved from 'https://clinicaltrials.gov/ct2/show/NCT02077959,' (9 pages).
"Pidilizumab Overview—Creative Biolabs," retreived from 'https://www.creativebiolabs.net/pidilizumab-overview.htm,' on Sep. 15, 2020, (2 pages). (See concurrently cited "EPO Letter Accompanying Subsequently Filed Items dated Dec. 22, 2021").
Menard et al., "Renal Cell Carcinoma (RCC) Tumors Display Large Expansion of Double Positive (DP) CD4+CD8+ T Cells With Expression of Exhaustion Markers," Frontiers in Immunology, vol. 9, pp. 1-13, 2018, (13 pages).
Hakkarainen et al., "CD40 Is Expressed on Ovarian Cancer Cells and Can Be Utilized for Targeting Adenoviruses1," Clinical Cancer Research, vol. 9, pp. 619-624, 2003, (7 pages).
Albuquerque et al., "Computationally-obtained structural insights into the molecular interactions between Pidilizumab and binding partners DLL1 and PD-1," Journal of Biomolecular Structure and Dynamics, pp. 1-13, 2021, (14 pages).
Waldmann, "The biology of interleukin-2 and interleukin-15: implications for cancer therapy and vaccine design," Nature Reviews Immunology, vol. 6, pp. 595-601, 2006, (7 pages).
Expert Declaration executed by David Bechard on Oct. 22, 2021, (4 pages).

* cited by examiner

IL-15 AND IL-15RALPHA SUSHI DOMAIN BASED IMMUNOCYTOKINES

This application claims priority to International Application No. PCT/EP2014/0021818, filed Aug. 8, 2014, and titled "IL-15 AND IL-15Ra SUSHI DOMAIN BASED MODULOKINES", which in turn claims the priority of the European patent application EP 13003963.9, filed on Aug. 8, 2013, both of which are herein incorporated by reference in their entireties.

FIELD OF THE INVENTION

The present invention relates to new "immunocytokines", called herein modulokines, and to their use as a medicine, in particular for the treatment of cancer, by activating tumor-infiltrating lymphocytes (TILs).

BACKGROUND

The vertebrate immune system requires multiple molecular and cellular interactions to achieve optimal immune responses against tumor.

Now, host anti-tumor immunity is mainly affected by TILs (GALON et al., Science, vol. 313, p: 1960-1964, 2006). In fact, multiple lines of evidence have indicated that TILs are subject to inhibitory regulation by tumor cells.

In order to "reactivate" said TILs, multiple strategies and targets have been envisaged. These strategies are based either on the i) inhibition of TILs immunosuppressive receptors (e.g. CTL-A4, PD-1, BTLA, LAG3 HAVCR2, ADORA2A, or inhibitory KIRs) for promoting immune activation by preventing downregulation signals; or on the ii) stimulation of TIL co-stimulatory receptors (e.g. CD40, 4-1BB, OX-40 or glucocorticoid-induced TNFR-related protein (GITR)), for promoting T and/or NK cells activation.

Even if said therapies have already provided some promising results, it seems that the efficiency of these strategies is limited. Most of the time, only a few percentage of the cohorts shows a restored TILs response.

In order to obtain reinforced efficiency, it is now envisaged to combine these strategies with other drugs or modulator.

Thus, the inventors try to combine these strategies with an anti-PD1 antibody with the modulator disclosed in patent application WO 2007/046006.

The results have shown that this combination was not able to restore a significant portion—i.e. about 20%—of TILs isolated from Renal Cell Carcinoma (RCC) patients.

SUMMARY OF THE INVENTION

Now, the inventors also tried another combination in which the same modulator was fused with the same antibody providing a new type of immunocytokines that they called "modulokines". Surprisingly, and as compared to the previous combination, this combination has provided a strong TILs reactivations, which reactivation was observed for most of the TILs—i.e. about 80%.

This strong synergy enable to envisage new therapies.

Consequently, the present invention relates to an immunocytokine comprising:

A) a conjugate, and
B) an immunomodulatory antibody or a fragment thereof directly or indirectly linked by covalence to said conjugate, wherein said conjugate comprises:

(i) a polypeptide comprising the amino acid sequence of interleukin 15 or derivatives thereof, and
(ii) a polypeptide comprising the amino acid sequence of the sushi domain of IL-15Rα or derivatives thereof In a second aspect, the invention relates to a nucleic acid encoding for an immunocytokine as described above.

In a third aspect, the present invention provides a vector comprising a nucleic acid as described above.

In a forth aspect, the present invention relates to a host cell genetically engineered with the polynucleotide or with the vector described previously. The present invention also relates to a method of producing a host cell genetically engineered expressing an immunocytokine according to the invention, said method comprising the steps of: (i) introducing in vitro or ex vivo a nucleic acid or a vector as described above into a host cell, (ii) culturing in vitro or ex vivo the recombinant host cell genetically engineered obtained and (iii), optionally, selecting the cells which express and/or secrete said immunocytokine.

In a preferred embodiment said host cell genetically engineered is an animal cell, and preferably a CHO cell.

In a fifth aspect, the present invention provides a pharmaceutical composition comprising the immunocytokine as described above, a nucleic acid encoding thereof, or a nucleic acid vector comprising said nucleic acid, eventually associated with a pharmaceutically acceptable carrier.

In a preferred embodiment, said composition comprises a further therapeutic agent, which is preferably an anticancer agent.

In a sixth aspect, the present invention relates to a pharmaceutical composition as described previously for treating cancer in a subject.

In seventh aspect, the present invention relates to the products containing:

(i) an immunocytokine as describe above, a nucleic acid sequence coding therefore, or a vector comprising such a nucleic acid sequence, and
(ii) a therapeutic agent, preferably an anticancer agent, as a combined preparation for simultaneous, separate, or sequential use for treating cancer in a subject.

In an eighth aspect, the present invention relates to a method for treating cancer in a subject comprising the step of administrating to said subject a pharmaceutical composition as described previously.

In a final aspect, the present invention relates to a method for treating cancer comprising the step of simultaneously, separately, or sequentially administrating to a subject in need thereof a therapeutically effective amount of:

(i) an immunocytokine as describe above, a nucleic acid sequence coding therefore, or a vector comprising such a nucleic acid sequence, and
(ii) a therapeutic agent, preferably an anticancer agent.

DETAILED DESCRIPTION

Figure 1:
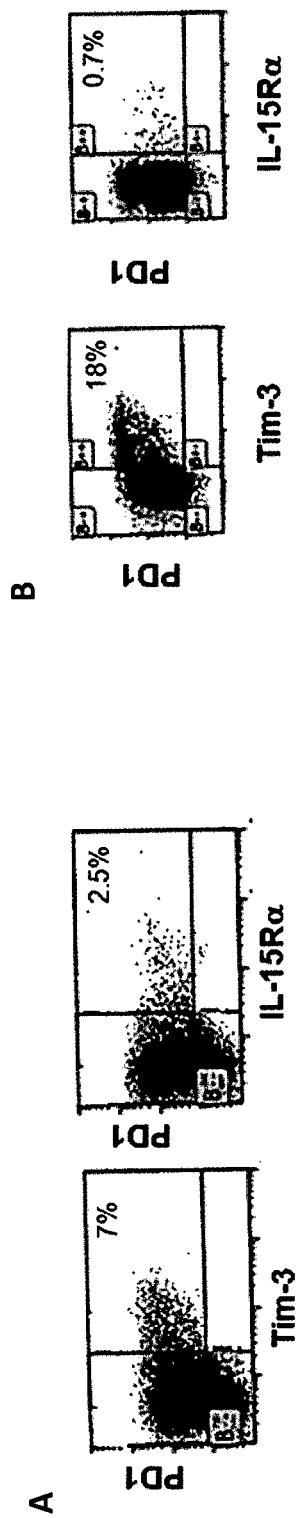
FIG. 1 shows PD-1, Tim-3 and IL-15Rα expression in TILs from patient A (A) and in patient B (B).

The term "immunocytokine" refers to a molecule comprising an antibody or fragments thereof directly or indirectly linked by covalence to a cytokine or derivatives thereof. Said antibody and said cytokine can be linked by a linker peptide.

Conjugate of the Immunocytokine of the Invention

The term "interleukin 15" in its general meaning in the art and refers to a cytokine with structural similarity to IL-2 (GRABSTEIN et al., Science, vol. 264(5161), p: 965-968, 1994). This cytokine is also known as IL-15, IL15 or MGC9721. This cytokine and IL-2 share many biological activities and they were found to bind common hematopoietin receptor subunits. Thus, they may compete for the same receptor, negatively regulating each other's activity. It has been established that IL-15 regulates T and natural killer cells activation and proliferation, and that the number of CD8+ memory cells is shown to be controlled by a balance between this cytokine and IL2. IL-15 activity can be measured by determining its proliferation induction on kit225 cell line (HORI et al., Blood, vol. 70(4), p: 1069-72, 1987), as disclosed in the Examples.

Said IL-15 or derivatives thereof have at least 10% of the activity of human interleukin-15 on the proliferation induction of kit225 cell line, preferably at least 25% and more preferably at least 50%.

Said interleukin 15 is a mammalian interleukin 15, preferably a primate interleukin 15, and more preferably a human interleukin 15.

Mammalian interleukin 15 can be simply identified by the skilled person. As an example, one can cite Interleukin 15 from *Sus scrofa* (Accession number ABF82250), from *Rattus norvegicus* (Accession number NP_037261), from *Mus musculus* (Accession number NP_032383), from *Bos Taurus* (Accession number NP_776515), from *Oryctolagus cuniculus* (Accession number NP_001075685), from *Ovies aries* (Accession number NP_001009734), from *Felis catus* (Accession number NP_001009207), from *Macaca fascicularis* (Accession number BAA19149), from *Homo sapiens* (Accession number NP_000576), from *Macaca Mulatta* (Accession number NP_001038196), from *Cavia porcellus* (Accession number NP_001166300), or from *Chlorocebus sabaeus* (Accession number ACI289).

As used herein, the term "mammalian interleukin 15" refers to the consensus sequence SEQ ID no. 1.

Primate interleukin 15 can be simply identified by the skilled person. As an example, one can cite Interleukin 15 from *Sus scrofa* (Accession number ABF82250), from *Oryctolagus cuniculus* (Accession number NP_001075685), from *Macaca fascicularis* (Accession number BAA19149), from *Homo sapiens* (Accession number NP_000576), from *Macaca Mulatta* (Accession number NP_001038196), or from *Chlorocebus sabaeus* (Accession number ACI289).

As used herein, the term "primate interleukin 15" refers to the consensus sequence SEQ ID no. 2.

Human interleukin 15 can be simply identify by the skilled person and refers to the amino acids sequence SEQ ID no. 3.

As used herein, the term "interleukin 15 derivatives" refers to an amino acid sequence having a percentage of identity of at least 92.5% (i.e. corresponding to about 10 amino acids substitutions) with an amino acid sequence selected in the group consisting of SEQ ID no: 1, SEQ ID no. 2 and SEQ ID no. 3, preferably of at least 96% (i.e. corresponding to about 5 amino acids substitutions), and more preferably of at least 98.5% (i.e. corresponding to about 2 amino acids substitutions) or of at least 99% i.e. corresponding to about 1 amino acid substitution). Such derivatives can be simply identified by the skilled person in view of its personal knowledge and of the teaching of the present patent application. As an example of such derivatives, one can cite those described in the International Patent Application PCT WO 2009/135031. It will also be understood that natural amino acids may be replaced by chemically modified amino acids. Typically, such chemically modified amino acids increase the polypeptide half life.

As used herein, "percentage of identity" between two amino acids sequences, means the percentage of identical amino-acids, between the two sequences to be compared, obtained with the best alignment of said sequences, this percentage being purely statistical and the differences between these two sequences being randomly spread over the amino acids sequences. As used herein, "best alignment" or "optimal alignment", means the alignment for which the determined percentage of identity (see below) is the highest. Sequences comparison between two amino acids sequences are usually realized by comparing these sequences that have been previously aligned according to the best alignment; this comparison is realized on segments of comparison in order to identify and compare the local regions of similarity. The best sequences alignment to perform comparison can be realized, beside by a manual way, by using the local homology algorithm developed by SMITH and WATERMAN (*Ad. App. Math.*, vol. 2, p: 482, 1981), by using the global homology algorithm developed by NEDDLEMAN and WUNSCH (*J. Mol. Biol.*, vol. 48, p: 443, 1970), by using the method of similarities developed by PEARSON and LIPMAN (*Proc. Natl. Acd. Sci. USA*, vol. 85, p: 2444, 1988), by using computer softwares using such algorithms (GAP, BESTFIT, BLAST P, BLAST N, FASTA, TFASTA in the Wisconsin Genetics software Package, Genetics Computer Group, 575 Science Dr., Madison, Wis. USA), by using the MUSCLE multiple alignment algorithms (Edgar, Robert C., *Nucleic Acids Research*, vol. 32, p: 1792, 2004), or by using CLUSTAL (GOUJON et al., Nucleic acids research, vol. 38, W695-9, 2010). To get the best local alignment, one can preferably use the BLAST software with the BLOSUM 62 matrix. The identity percentage between two sequences of amino acids is determined by comparing these two sequences optimally aligned, the amino acids sequences being able to encompass additions or deletions in respect to the reference sequence in order to get the optimal alignment between these two sequences. The percentage of identity is calculated by determining the number of identical position between these two sequences, and dividing this number by the total number of compared positions, and by multiplying the result obtained by 100 to get the percentage of identity between these two sequences.

Preferably, the interleukin 15 derivatives are IL-15 agonist or superagonist. One skilled in the art can simply identified an IL-15-agonist or -superagonist. As a example of IL-15-agonist or -superagonist, one can cite the ones disclosed in the International patent application WO 2005/085282 or in ZHU et al. (*J. Immunol.*, vol. 183(6), p: 3598-607, 2009).

Still preferably, said IL-15 agonist or superagonist is selected in the group comprising/consisting of L45D, L45E, S51D, L52D, N72D, N72E, N72A, N72S, N72Y and N72P (in reference to sequence of human IL-15, SEQ ID no. 3).

As used herein the term "the sushi domain of IL-15Rα" has its general meaning in the art and refers to a domain beginning at the first cysteine residue (C1) after the signal peptide of IL-15Rα, and ending at the fourth cysteine residue (C4) after said signal peptide. Said sushi domain corresponding to a portion of the extracellular region of IL-15Rα is necessary for its binding to IL-15 (WEI et al., *J. Immunol.*, vol. 167(1), p: 277-282, 2001).

Said sushi domain of IL-15Rα or derivatives thereof has at least 10% of the binding activity of the sushi domain of human IL-15Rα to human interleukin-15, preferably at least 25% and more preferably at least 50%. Said binding activity can be simply determined by the method disclosed in WEI et al. (abovementioned, 2001).

Said sushi domain of the IL-15Rα is the sushi domain of a mammalian IL-15Rα, preferably the sushi domain of a primate IL-15Rα and more preferably the sushi domain of the human IL-15Rα.

The sushi domain of a mammalian IL-15Rα can be simply identified by the skilled person. As an example, one can cite the sushi domain of a IL-15Rα from *Rattus norvegicus* (Accession number XP_002728555), from *Mus musculus* (Accession number EDL08026), from *Bos Taurus* (Accession number XP_002692113), from *Oryctolagus cuniculus* (Accession number XP_002723298), from *Macaca fascicularis* (Accession number ACI42785), from *Macaca nemestrina* (Accession number ACI42783), from *Homo sapiens* (Accession number Q13261.1), from *Macaca Mulatta* (Accession number NP_001166315), *Pongo abelii* (Accession number XP_002820541), *Cercocebus torquatus* (Accession number ACI42784), *Callithrix jacchus* (Accession number XP_002750073), or from *Cavia porcellus* (Accession number NP_001166314).

As used herein, the term "sushi domain of a mammalian IL-15Rα" refers to the consensus sequence SEQ ID no. 4.

Preferably, the polypeptide comprising the amino acid sequence of the sushi domain of a mammalian IL-15Rα refers to the consensus sequence SEQ ID no. 5.

The sushi domain of a primate IL-15Rα can be simply identified by the skilled person. As an example, one can cite sushi domains of IL-15Rα from *Oryctolagus cuniculus*, from *Macaca fascicularis*, from *Macaca nemestrina*, from *Homo sapiens*, from *Macaca Mulatta, Pongo abelii, Cercocebus torquatus*, or *Callithrix jacchus*.

As used herein, the term "sushi domain of a primate IL-15Rα" refers to the consensus sequence SEQ ID no. 6.

Preferably, the polypeptide comprising the amino acid sequence of the sushi domain of a primate IL-15Rα refers to the consensus sequence SEQ ID no. 7.

The sushi domain of human IL-15Rα can be simply identified by the skilled person and refers to the amino acids sequence SEQ ID no. 8.

Preferably, the polypeptide comprising the amino acid sequence of the sushi domain of human IL-15Rα refers to SEQ ID no. 9.

As used herein, the term "derivatives of the sushi domain of the IL-15Rα" refers to an amino acid sequence having a percentage of identity of at least 92% (i.e. corresponding to about 5 amino acids substitutions) with an amino acid sequence selected in the group consisting of SEQ ID no: 4, SEQ ID no. 5, SEQ ID no. 6, SEQ ID no: 7, SEQ ID no. 8, and SEQ ID no. 9, preferably of at least 96% (i.e. corresponding to about 2 amino acids substitutions), and more preferably of at least 98% (i.e. corresponding to about 1 amino acids substitutions). Such derivatives comprise the four cysteine residues of the sushi domain of L-15Rα and can be simply identified by the skilled person in view of his/her general knowledge and of the teaching of the present patent application. It will also be understood that natural amino acids may be replaced by chemically modified amino acids. Typically, such chemically modified amino acids enable to increase the polypeptide half life.

According to a preferred embodiment, the conjugate comprises (ii) a polypeptide comprising the amino acid sequence of the sushi and hinge domains of IL-15Rα or derivatives thereof.

The IL-15Rα hinge domain is defined as the amino acid sequence that begins at the first amino residue after the sushi domain and that ends at the last amino acid residue before the first potential site of glycosylation. In human IL-15Rα, the amino acid sequence of the hinge region consists of the fourteen amino acids which are located after the sushi domain of this IL-15Ralpha, in a C-terminal position relative to said sushi domain, i.e., said IL-15Ralpha hinge region begins at the first amino acid after said (C4) cysteine residue, and ends at the fourteenth amino acid (counting in the standard "from N-terminal to C-terminal" orientation).

Said sushi and hinge domains of IL-15Rα are the sushi and hinge domains of a mammalian IL-15Rα, preferably the sushi and hinge domains of a primate IL-15Rα and more preferably the sushi and hinge domains of the human IL-15Rα.

The amino acid sequence of the sushi and hinge domains of a mammalian IL-15Rα can be simply identified by the skilled person. As used herein, the term "sushi and hinge domains of a mammalian IL-15Rα" refers to the consensus sequence SEQ ID no. 10.

The amino acid sequence of the sushi and hinge domains of a primate IL-15Rα can be simply identified by the skilled person. As used herein, the term "sushi and hinge domains of a primate IL-15Rα" refers to the consensus sequence SEQ ID no. 11.

The amino acid sequence of the sushi and hinge domains of human IL-15Rα can be simply identified by the skilled person. As used herein, the term "sushi and hinge domains of human IL-15Rα" refers to the consensus sequence SEQ ID no. 12.

As used herein, the term "derivatives of the sushi and hinge domains of IL-15Rα" refers to an amino acid sequence having a percentage of identity of at least 93% (i.e. corresponding to about 5 amino acids substitutions) with an amino acid sequence selected in the group consisting of SEQ ID no: 10, SEQ ID no. 11, and SEQ ID no. 12, preferably of at least 97% (i.e. corresponding to about 2 amino acids substitutions), and more preferably of at least 98% (i.e. corresponding to about 1 amino acids substitution). Such derivatives comprise the four cysteine residues of the sushi domain of L-15Rα and can be simply identified by the skilled person in view of its general knowledge and of the teaching of the present patent application. It will also be understood that natural amino acids may be replaced by chemically modified amino acids. Typically, such chemically modified amino acids enable to increase the polypeptide half life.

Both polypeptides i) and ii) of the conjugate may be linked non-covalently such as in the complex disclosed in U.S. Pat. No. 8,124,084 B2. Said conjugate or complex can be simply obtained by providing a suitable amount of the polypeptide i), providing a suitable amount of the polypeptide ii), admixing both polypeptides under suitable pH and ionic conditions for a duration sufficient to allow complex (i.e. conjugate) formation, and optionally concentrating or purifying said complex. The polypeptides of the complex (i.e. conjugate) can be formed, for example, using a peptide synthesizer according to standard methods; by expressing each polypeptide separately in a cell or cell extract, then isolating and purifying the polypeptide. Optionally, the therapeutic polypeptide complex of the invention can be formed by expressing both polypeptides i) and ii) in the same cell or cell extract, then isolating and purifying the complexes, for example, using chromatographic techniques, such as affinity chromatography with antibodies to the lymphokine portion, the lymphokine receptor portion, or to the complex.

Both polypeptides i) and ii) of the conjugate may be also covalently linked using bifunctional protein coupling agents or in a fusion protein.

Bifunctional protein coupling agents are well known from the skilled person such as methods using them, and include, as examples, N-succinimidyl (2-pyridyldithio) propionate (SPDP), succinimidyl (N-maleimidomethyl) cyclohexane-1-carboxylate, iminothiolane (IT), bifunctional derivatives of imidoesters (such as dimethyl adipimidate HCL), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene).

The term "fusion protein" refers to a protein created through the joining of two or more genes which originally coded for separate proteins. It is also known as a chimeric protein. Translation of this fusion gene results in a single polypeptide with functional properties deriving from each of the original proteins. Recombinant fusion proteins are created artificially by recombinant DNA technology for use in biological research or therapeutics. A recombinant fusion protein is a protein created through genetic engineering of a fusion gene. This typically involves removing the stop codon from a cDNA sequence coding for the first protein, then appending the cDNA sequence of the second protein in frame through ligation or overlap extension PCR. That DNA sequence will then be expressed by a cell as a single protein. The protein can be engineered to include the full sequence of both original proteins, or only a portion of either.

In a preferred embodiment, the conjugate is a fusion protein.

The amino acid sequence of interleukin 15 or derivatives thereof can be in a C-terminal or in an N-terminal position relative to the amino acid sequence of the sushi domain of IL-15Rα or derivatives thereof. Preferably, the amino acid sequence of the interleukin 15 or derivatives thereof is in a C-terminal position relative to the amino acid sequence of the sushi domain of IL-15Rα or derivatives thereof.

The amino acid sequence of interleukin 15 or derivatives thereof and the amino acid sequence of the sushi domain of IL-15Rα or derivatives thereof may be separated by a first "linker" amino acid sequence. Said first "linker" amino acid sequence may be of a length sufficient to ensure that the fusion protein form proper secondary and tertiary structures.

The length of the first linker amino acid sequence may vary without significantly affecting the biological activity of the fusion protein. Typically, the first linker amino acid sequence comprises at least one, but less than 30 amino acids e.g., a linker of 2-30 amino acids, preferably of 10-30 amino acids, more preferably of 15-30 amino acids, still more preferably of 15-25 amino acids, most preferably of 18-22 amino acids.

Preferred linker amino acid sequences are those which allow the conjugate to adopt a proper conformation (i.e., a conformation allowing a proper signal transducing activity through the IL-15Rbeta/gamma signaling pathway).

The most suitable first linker amino acid sequences (1) will adopt a flexible extended conformation, (2) will not exhibit a propensity for developing ordered secondary structure which could interact with the functional domains of fusion proteins, and (3) will have minimal hydrophobic or charged character which could promote interaction with the functional protein domains.

Preferably, the first linker amino acid sequence comprises near neutral amino acids selected in the group comprising Gly (G), Asn (N), Ser (S), Thr (T), Ala (A), Leu (L), and Gln (Q), most preferably in the group comprising Gly (G), Asn (N), and Ser (S).

Examples of linker sequences are described in U.S. Pat. Nos. 5,073,627 and 5,108,910.

Illustrative flexible linkers that are more particularly suitable for the present invention include those coded by the sequences of SEQ ID NO: 13 (SGGSGGGGSGGGSGGGSLQ), SEQ ID no. 14 (SGGSGGGGSGGGSGGGSGG) or SEQ ID no. 15 (SGGGSGGGGSGGGGSGGGSLQ).

Preferably, the conjugate has the sequence SEQ ID no. 18 or SEQ ID no. 19.

Antibody of the Immunocytokine of the Invention

The term "antibody" refers to an immunoglobulin molecule corresponding to a tetramer comprising four polypeptide chains, two identical heavy (H) chains (about 50-70 kDa when full length) and two identical light (L) chains (about 25 kDa when full length) inter-connected by disulfide bonds. Light chains are classified as kappa and lambda. Heavy chains are classified as gamma, mu, alpha, delta, or epsilon, and define the antibody's isotype as IgG, IgM, IgA, IgD, and IgE, respectively. Each heavy chain is comprised of a N-term heavy chain variable region (abbreviated herein as HCVR) and a heavy chain constant region. The heavy chain constant region is comprised of three domains (CH1, CH2, and CH3) for IgG, IgD, and IgA; and 4 domains (CH1, CH2, CH3, and CH4) for IgM and IgE. Each light chain is comprised of a N-term light chain variable region (abbreviated herein as LCVR) and a light chain constant region. The light chain constant region is comprised of one domain, CL. The HCVR and LCVR regions can be further subdivided into regions of hypervariability, termed complementarity determining regions (CDRs), interspersed with regions that are more conserved, termed framework regions (FR). Each HCVR and LCVR is composed of three CDRs and four FRs, arranged from amino-terminus to carboxy-terminus in the following order: FR1, CDR1, FR2, CDR2, FR3, CDR3, FR4. The assignment of amino acids to each domain is in accordance with well-known conventions. The functional ability of the antibody to bind a particular antigen depends on the variable regions of each light/heavy chain pair, and is largely determined by the CDRs.

The term "antibody", as used herein, refers to a monoclonal antibody per se. A monoclonal antibody can be a human antibody, chimeric antibody and/or humanized antibody.

Advantageously, the term antibody refers to an IgG, such as IgG1, IgG2 (IgG2a or IgG2b), IgG3 and IgG4. Preferably, the term antibody refers to IgG1 or IgG2, and more preferably to IgG2a.

"Chimeric antibody" means an antibody that is composed of variables regions from a murine immunoglobulin and of constant regions of a human immunoglobulin. This alteration consists simply of substituting the constant region of a human antibody with the murine constant region, thus resulting in a human/murine chimera which may have sufficiently low immunogenicity to be acceptable for pharmaceutical use. A number of methods for producing such chimeric antibodies have yet been reported, thus forming part of the general knowledge of the skilled artisan (See, e.g., U.S. Pat. No. 5,225,539).

"Humanized antibody" means an antibody that is composed partially or fully of amino acid sequences derived from a human antibody germline by altering the sequence of an antibody having non-human complementarity determining regions (CDR). This humanization of the variable region of the antibody and eventually the CDR is made by techniques that are by now well known in the art. As an example, British Patent Application GB 2188638A and U.S. Pat. No. 5,585,089 disclose processes wherein recombinant antibodies are produced where the only portion of the antibody that is substituted is the complementarity determining region, or "CDR". The CDR grafting technique has been used to generate antibodies which consist of murine CDRs, and human variable region framework and constant regions (See. e. g., RIECHMANN et al., Nature, vol. 332, p: 323-327, 1988). These antibodies retain the human constant regions that are necessary for Fc dependent effector function, but are much less likely to evoke an immune response against the antibody. As an example, the framework regions of the variable regions are substituted by the corresponding human framework regions leaving the non-human CDR substantially intact, or even replacing the CDR with sequences derived from a human genome. Fully human antibodies are produced in genetically modified mice whose immune systems have been altered to correspond to human immune systems. As mentioned above, it is sufficient for use in the methods of the invention, to employ an immunologically specific fragment of the antibody, including fragments representing single chain forms.

A humanized antibody again refers to an antibody comprising a human framework, at least one CDR from a non-human antibody, and in which any constant region present is substantially identical to a human immunoglobulin constant region, i. e., at least about 85 or 90%, preferably at least 95% identical. Hence, all parts of a humanized antibody, except possibly the CDRs, are substantially identical to corresponding parts of one or more native human immunoglobulin sequences. For example, a humanized immunoglobulin would typically not encompass a chimeric mouse variable region/human constant region antibody. As an example, the design of humanized immunoglobulins may be carried out as follows: when an amino acid falls under the following category, the framework amino acid of a human immunoglobulin to be used (acceptor immunoglobulin) is replaced by a framework amino acid from a CDR-providing non-human immunoglobulin (donor immunoglobulin): (a) the amino acid in the human framework region of the acceptor immunoglobulin is unusual for human immunoglobulin at that position, whereas the corresponding amino acid in the donor immunoglobulin is typical for human immunoglobulin at that position; (b) the position of the amino acid is immediately adjacent to one of the CDRs; or (c) any side chain atom of a framework amino acid is within about 5-6 angstroms (center-to-center) of any atom of a CDR amino acid in a three dimensional immunoglobulin model (QUEEN et al., Proc. Natl. Acad. Sci. USA, vol. 88, p: 2869, 1991). When each of the amino acids in the human framework region of the acceptor immunoglobulin and a corresponding amino acid in the donor immunoglobulin is unusual for human immunoglobulin at that position, such an amino acid is replaced by an amino acid typical for human immunoglobulin at that position.

The term "antibody fragment" as used herein refers to antibody fragment capable of reacting with the same antigen than its antibody counterpart. Such fragments can be simply identified by the skilled person and comprise, as an example, $F_{ab}$ fragment (e.g., by papain digestion), $F_{ab}'$ fragment (e.g., by pepsin digestion and partial reduction), $F(_{ab}')_2$ fragment (e.g., by pepsin digestion), $F_{acb}$ (e.g., by plasmin digestion), $F_d$ (e.g., by pepsin digestion, partial reduction and reaggregation), and also $scF_v$ (single chain Fv; e.g., by molecular biology techniques) fragment are encompassed by the invention.

Such fragments can be produced by enzymatic cleavage, synthetic or recombinant techniques, as known in the art and/or as described herein. Antibodies can also be produced in a variety of truncated forms using antibody genes in which one or more stop codons have been introduced upstream of the natural stop site. For example, a combination gene encoding a $F(_{ab}')_2$ heavy chain portion can be designed to include DNA sequences encoding the $CH_1$ domain and/or hinge region of the heavy chain. The various portions of antibodies can be joined together chemically by conventional techniques, or can be prepared as a contiguous protein using genetic engineering techniques.

Preferably, said antibody fragment is a scFv fragment.

The term "immunomodulatory antibody", as used herein, refers to an antibody acting either by:

1) inhibiting an immunosuppressive receptor such as CTL-A4, PD-1, BTLA, LAG3 HAVCR2, ADORA2A, or inhibitory KIRs, either by binding this receptor or its ligand, thus promoting immune activation by preventing downregulation signals; or 2) stimulating a co-stimulatory receptor such as CD40, CD137, CD134 or TNFRSF18 (GITR), thus promoting T and/or NK cells activation.

In a first preferred embodiment, the immunomodulatory antibody inhibits an immunosuppressive receptor. As an example of immunomodulatory antibodies inhibiting immunosuppressive receptors, one can cite CTL-A4, inhibitory KIRs, BTLA, LAG3 HAVCR2, ADORA2A, and PD-1 antagonists, and still preferably PD-1 antagonists selected among anti-PD1 and anti-PD-L1 antibodies.

CTL-A4 (Cytotoxic Lymphocyte Associated Antigen, also designated CD 152) was discovered in 1987 (BRUNET et al., Nature, vol. 328, p: 267-270, 1987). The role of CTL-A4 is primarily to inhibit T cell activation and this was shown in CTL-A4 deficient mice suffering from massive lymphoproliferation (CHAMBERS et al., Immunity, vol. 7, p: 8855-8959, 1997). Now, the blockage of CTL-A4 has been shown to enhance T cell responses in vitro (WALUNAS et al., Immunity, vol. 1, p: 405-413, 1994) and in vivo (KEARNEY, J. Immunol, vol. 155, p: 1032-1036, 1995) and also to increase antitumour immunity (LEACH, Science, vol. 271, p: 1734-1736, 1996). As an example of antibodies corresponding to CTL-A4 antagonists, one can cite ipilimumab (also referred to as MDX-010 and 10D1, available from MEDAREX, and marketed as YERVOY™ by BRISTOL-MYERS SQUIBB COMPANY) disclosed in WO 01/14424, ticilimumab (also known as 11.2.1 and CP-675, 206) disclosed in WO 00/37504, and also the CTL-A4 antibodies disclosed in International patent applications WO 98/42752, WO 01/14424, WO 2004/035607, and WO 2012/120125, in EP 1212422 and EP 1262193, in U.S. Pat. Nos. 5,811,097, 5,855,887, 5,977,318, 6,051,227, 6,207,156, 6,682,736, 6,984,720, 7,109,003, and 7,132,281, which are herein incorporated by reference.

Programmed Cell Death 1 also known as PD-1 (also referred to as PDCD1 or CD279) is a ~55 kD type I membrane glycoprotein. PD-1 is a receptor of the CD28 costimulatory gene family, which is moderately expressed on naive T, B and NK cells and up-regulated by T/B cell receptor signaling on lymphocytes, monocytes and myeloid cells. PD-1 has two known ligands with distinct expression profiles, PD-L1 (B7-H1), which is widely expressed—i.e. on naive lymphocytes on activated B and T cells, monocytes and dendritic cells—and PD-L2 (B7-DC), whose expression is restricted—i.e. on activated dendritic cells, macrophages and monocytes and on vascular endothelial cells-. In several murine syngeneic tumor models, blockade of either PD-1 or PD-L1 significantly inhibited tumor growth or induced complete regression. Thus, the PD-1 is recognized as an important player in immune regulation and the maintenance of peripheral tolerance. As an example of antibodies corresponding to PD-1 antagonists, one can cite nivolumab (also known as BMS-936558 or MDX1106; anti-PD-1 antibody, BRISTOL-MYERS SQUIBB) is disclosed in WO2006/121168, Merck 3745 (also known as MK-3475 or SCH-900475, is an anti-PD-1 antibody) is disclosed in WO2009/114335, CT-01 1 (also known as hBAT or hBAT-1, anti-PD-1 antibody) is disclosed in WO2009/101611, lambrolizumab is disclosed in WO2008/156712, AMP514 which is disclosed in WO2010/027423, WO2010/027827, WO2010/027828, and WO2010/098788, and also the antibodies disclosed in International patent applications WO 2004/056875, WO 2006/056875, WO 2008/083174, WO2010/029435, WO2010/036959, WO2010/089411, WO2011/110604, WO2012/135408, and WO2012/145493. Said PD-1 antagonist may correspond to an anti-PD-L1 antibody such as MDX-1 105 (also known as BMS-936559, anti-PD-L1 antibody) disclosed in WO 2007/005874, or YW243.55.S70 (also known as MPDL3280A or RG7446; anti-PD-L1 antibody) disclosed in WO 2010/077634, which are herein incorporated by reference.

Killer-cell immunoglobulin-like receptors (KIRs), are a family of cell surface proteins found on important cells of the immune system called natural killer (NK) cells. They regulate the killing function of these cells by interacting with MHC class I molecules, which are expressed on all cell types. This interaction allows them to detect virally infected cells or tumor cells that have a characteristic low level of Class I MHC on their surface. Most KIRs are inhibitory, meaning that their recognition of MHC suppresses the cytotoxic activity of their NK cell. Only a limited number of KIRs have the ability to activate cell.

Inhibitory KIRs have a long cytoplasmic tail containing Immunoreceptor Tyrosine-based Inhibitory Motif (ITIM), which transduce inhibitory signals to the NK cell upon engagement of their MHC class I ligands. The known inhibitory KIRs include members of the KIR2DL and KIR3DL subfamilies comprising KIR2DL1, KIR2DL2, KIR2DL3, KIR2DL4, KIR2DL5A, KIR2DL5B, KIR3DL1, KIR3DL2, and KIR3DL3. As an example of antibodies corresponding to inhibitory KIRs antagonists, one can cite the antibody 1-7F9 disclosed in WO 2006/003179, which is herein incorporated by reference.

BTLA (B- and T-lymphocyte attenuator), also known as CD272, is induced during activation of T cells, and remains expressed on Th1 cells but not Th2 cells. BTLA displays T-Cell inhibition via interaction with tumor necrosis factor (receptor), member 14 (TNFRSF14), also known as herpes virus entry mediator (HVEM), TR2; ATAR; HVEA; CD270; LIGHTR. TNFRSF14 was identified as a cellular mediator of herpes simplex virus (HSV) entry. The cytoplasmic region of this receptor was found to bind to several TRAF family members, which may mediate the signal transduction pathways that activate the immune response. Finally, the BTLA/HVEM complexes negatively regulate T-cell immune responses. As an example of BTLA/HVEM antagonist, one can cite the antibodies disclosed in WO 2008/076560, WO 2010/106051, and WO 2011/014438.

LAG3 (Lymphocyte-activation gene 3, also known as CD223) belongs to immunoglobulin (Ig) superfamily and contains 4 extracellular Ig-like domains. As an example of LAG3 antagonists, one can cite the antibodies disclosed in WO 2010/019570.

HAVCR2 (Hepatitis A virus cellular receptor 2, also known as Tim-3, KIM-3; TIMD3; Tim-3; and TIMD-3) is a Th1-specific cell surface protein belonging to the immunoglobulin superfamily. HAVCR2 regulates macrophage activation and inhibits Th1-mediated auto- and alloimmune responses, thus promoting immunological tolerance. As an example of HAVCR2 antagonists, one can cite the antibodies disclosed in WO 2013/006490A.

ADORA2A (adenosine $A_{2A}$ receptor, also known as A2aR, RDC8; or ADORA2) belongs to the guanine nucleotide-binding protein (G protein)-coupled receptor (GPCR) superfamily, which is subdivided into classes and subtypes. This protein plays an important role in many biological functions, such as cardiac rhythm and circulation, cerebral and renal blood flow, immune function, pain regulation, and sleep. It has been implicated in pathophysiological conditions such as inflammatory diseases and neurodegenerative disorders.

In a second preferred embodiment, the immunomodulatory antibody stimulates a co-stimulatory receptor.

As an example of immunomodulatory antibodies stimulating co-stimulatory receptors, one can cite CD40, CD137, CD134 and TNFRSF18 agonists.

CD40 is a member of the TNF-receptor superfamily found on APC, which is required for their activation. This receptor has been found to be essential in mediating a broad variety of immune and inflammatory responses including T cell-dependent immunoglobulin class switching, and memory B cell development.

As an example of antibodies corresponding to CD40 agonists, one can cite those disclosed in WO 03/040170, in WO 2005/063981, in WO 2005/063289 and in WO 2012/041635, which are herein incorporated by reference.

CD137 is a member of the tumor necrosis factor (TNF) receptor family. Its alternative names are tumor necrosis factor receptor superfamily member 9 (TNFRSF9), 4-1BB and induced by lymphocyte activation (ILA). CD137 can be expressed by activated T cells, but to a larger extent on CD8 than on CD4 T cells. In addition, CD 137 expression is found on dendritic cells, follicular dendritic cells, natural killer cells, granulocytes and cells of blood vessel walls at sites of inflammation. The best characterized activity of CD137 is its co-stimulatory activity for activated T cells. Crosslinking of CD137 enhances T cell proliferation, IL-2 secretion survival and cytolytic activity. Further, it can enhance immune activity to eliminate tumors in mice.

As an example of antibodies corresponding to CD137 agonists, one can cite urelumab (also known as BMS-663513), and the antibodies disclosed in WO 03/040170, WO 2004/010947, in WO 2005/035584, WO 2006/126835, and in WO 2012/145183, which are herein incorporated by reference.

CD134, also known as OX40, is a member of the TNFR-superfamily of receptors. OX40 is a costimulatory molecule, whose expression of OX40 is dependent on full activation of the T cell. OX40 binds to receptors on T-cells, preventing them from dying and subsequently increasing cytokine production. OX40 has a critical role in the maintenance of an immune response beyond the first few days and onwards to a memory response due to its ability to enhance survival.

As an example of antibodies corresponding to CD134 agonists, one can cite the antibodies disclosed in WO 2009/079335, in WO 2012/027328, WO 2013/038191, and in WO 2013/028231, which are herein incorporated by reference.

Tumor necrosis factor receptor superfamily member 18 (TNFRSF18) also known as activation-inducible TNFR family receptor (AITR) or glucocorticoid-induced TNFR-related protein (GITR) is a member of the tumor necrosis factor receptor (TNF-R) superfamily. This protein is a surface receptor molecule that has been shown to be involved in inhibiting the suppressive activity of T-regulatory cells and extending the survival of T-effector cells.

As an example of antibodies corresponding to TNFRSF18 agonists, one can cite the antibodies disclosed in WO 2006/105021, and in WO 2011/028683.

Both conjugate and antibody or fragment thereof may be covalently linked using bifunctional protein coupling agents or in a fusion protein.

Bifunctional protein coupling agents methods are well known by the skilled person and have been previously disclosed. As an example, the skilled person can use the method disclosed in TILL et al. (*Proc. Natl. Acad. U.S.A.*, vol. 86(6), p: 1987-91, 1989)

In a preferred embodiment, the immunocytokine is a fusion protein.

In another preferred embodiment, the immunocytokine is a complex, preferably a complex comprising a conjugate between the polypeptides i) and ii), wherein the polypeptide i) or ii) is fused to an antibody or fragment thereof.

The polypeptide i), the polypeptide ii), or the conjugate can be in a C-terminal or in an N-terminal position relative to the amino acid sequence of the antibody or fragment thereof.

Preferably, the conjugate is a fusion protein and the amino acid sequence of the conjugate is in a C-terminal position relative to the amino acid sequence of the antibody or fragment thereof, most preferably in a C-terminal position relative to the amino acid sequence of at least one of the heavy chain constant region of the antibody or fragment thereof.

The amino acid sequence of the conjugate and the amino acid sequence of the antibody or fragment thereof may be separated or not by a second "linker" amino acid sequence.

In a particular embodiment, the immunocytokine of the invention is a fusion protein wherein the conjugate and the antibody or fragment thereof, are not separated by any linker.

As for the first linker amino acid sequence, said second "linker" amino acid sequence may be of a length sufficient to ensure that the fusion protein form proper secondary and tertiary structures.

The length of the first linker amino acid sequence may vary without significantly affecting the biological activity of the fusion protein. Typically, the first linker amino acid sequence comprises at least one, but less than 30 amino acids e.g., a linker of 2-30 amino acids, preferably of 10-30 amino acids, more preferably of 15-30 amino acids, most preferably of 15-25 amino acids.

As for the first linker amino acid sequence, the most suitable second linker amino acid sequences (1) will adopt a flexible extended conformation, (2) will not exhibit a propensity for developing ordered secondary structure which could interact with the functional domains of fusion proteins, and (3) will have minimal hydrophobic or charged characteristics which could promote interaction with the functional protein domains.

Preferably, the second linker amino acid sequence comprises near neutral amino acid selected in the group comprising Gly (G), Asn (N), Ser (S), Thr (T), Ala (A), Leu (L), and Gln (Q), most preferably in the group comprising Gly (G), Asn (N), and Ser (S).

As an example of a second linker amino acid sequence which is suitable for the present invention, one can cite the sequence SEQ ID no. 16 (SGGGGSGGGGSGGGGSGGGGSG) or SEQ ID no. 17 (AAGGGSGGGSGGGGSGGGGSAA).

Nucleic Acids, Vectors and Recombinant Host Cells

In a second aspect the present invention relates to a nucleic acid encoding for a immunocytokine as described above, preferably an immunocytokine corresponding to a fusion protein.

Said nucleic acid corresponds to RNA or DNA, preferably to DNA.

According to a preferred embodiment, the nucleic acid encoding the immunocytokine of the invention is operatively linked to a gene expression sequence, which directs the expression of the nucleic acid within a prokarotic or an eukaryotic cell, preferably within an eukaryotic cell. The "gene expression sequence" is any regulatory nucleotide sequence, such as a promoter sequence or promoter-enhancer combination, which facilitates the efficient transcription and translation of the immunocytokine nucleic acid to which it is operatively linked. The gene expression sequence may, for example, be a mammalian or viral promoter, such as a constitutive or inducible promoter.

Constitutive mammalian promoters include, but are not limited to, the promoters for the following genes: hypoxanthine phosphoribosyl transferase (HPTR), adenosine deaminase, pyruvate kinase, beta.-actin promoter, muscle creatine kinase promoter, human elongation factor promoter and other constitutive promoters. Exemplary viral promoters which function constitutively in eukaryotic cells include, for example, promoters from the simian virus (e.g., SV40), papilloma virus, adenovirus, human immunodeficiency virus (HIV), cytomegalovirus (CMV), Rous sarcoma virus (RSV), hepatitis B virus (HBV), the long terminal repeats (LTR) of Moloney leukemia virus and other retroviruses, and the thymidine kinase promoter of herpes simplex virus. Other constitutive promoters are known to those of ordinary skill in the art.

The promoters useful as gene expression sequences of the invention also include inducible promoters. Inducible promoters are expressed in the presence of an inducing agent. For example, the metallothione in promoter is induced to promote transcription and translation in the presence of certain metal ions. Others inducible promoters are known to those of ordinary skill in the art.

In general, the gene expression sequence shall include, as necessary, 5' non-transcribing and 5' non-translating sequences involved with the initiation of transcription and translation, respectively, such as a TATA box, capping sequence, CAAT sequence, and the like. Especially, such 5' non-transcribing sequences will include a promoter region which includes a promoter sequence for transcriptional control of the operationally joined nucleic acid. The gene expression sequences optionally include enhancer sequences or upstream activator sequences as desired. As used herein, the nucleic acid sequence encoding the immunocytokine of the invention and the gene expression sequence are said to be "operationally linked" when they are covalently linked in such a way as to place the expression or transcription and/or translation of the immunocytokine of the invention coding sequence under the influence or control of the gene expression sequence.

Two DNA sequences are said to be operationally linked if induction of a promoter in the 5' gene expression sequence results in the transcription of the immunocytokine of the invention and if the nature of the linkage between the two DNA sequences does not (1) result in the introduction of a frame-shift mutation, (2) interfere with the ability of the promoter region to direct the transcription of the immunocytokine of the invention, or (3) interfere with the ability of the corresponding RNA transcript to be translated into a protein. Thus, a gene expression sequence would be operationally linked to a nucleic acid sequence coding for the immunocytokine of the invention if the gene expression sequence were capable of effecting transcription of that nucleic acid sequence such that the resulting transcript is translated into the desired polypeptide.

Advantageously, said nucleic acid sequence comprises an intron, since pre-mRNA molecules has often been demonstrated to improve production yields of recombinant molecules. Any sequences of intron may be sued, and as an example, one can cite tone ones disclosed in ZAGO et al. (*Biotechnol. Appl. Biochem.*, vol. 52(Pt 3), p: 191-8, 2009) and in CAMPOS-DA-PAZ et al. (*Mol. Biotechnol.*, vol. 39(2), p: 155-8, 2008).

The nucleic acid coding for the immunocytokine of the invention may be delivered in vivo alone or in association with a vector.

In a third aspect, the present invention relates to a vector comprising a nucleic acid as described above.

In its broadest sense, a "vector" is any vehicle capable of facilitating the transfer of the nucleic acid coding for the immunocytokine of the invention to the cells. Preferably, the vector transports the nucleic acid to cells with reduced degradation relative to the extent of degradation that would result in the absence of the vector. In general, the vectors useful in the invention include, but are not limited to, plasmids, cosmids, phagmids, episomes, artificial chromosomes, viruses, other vehicles derived from viral or bacterial sources that have been manipulated by the insertion or incorporation of the immunocytokine nucleic acid sequences.

Plasmid vectors are a preferred type of vector and have been extensively described in the art and are well known to those of skill in the art. See e.g., SANBROOK et al., "Molecular Cloning: A Laboratory Manual," Second Edition, Cold Spring Harbor Laboratory Press, 1989. Not limiting examples of plasmids include pBR322, pUC18, pUC19, pRC/CMV, SV40, and pBlueScript, and other plasmids are well known to those of ordinary skill in the art. Additionally, plasmids may be custom designed using restriction enzymes and ligation reactions to remove and add specific fragments of DNA.

Preferably, the nucleic acid vector can include selectable markers that are active both in bacteria and in mammalian cells.

In a forth aspect, the present invention relates to a host cell genetically engineered with the nucleic acid or with the vector described previously.

As used herein, the term "host cell genetically engineered" relates to host cells which have been transduced, transformed or transfected with the nucleic acid or with the vector described previously.

As representative examples of appropriate host cells, one can cite bacterial cells, such as *E. coli*, fungal cells such as yeast, insect cells such as Sf9, animal cells such as CHO or COS, plant cells, etc. The selection of an appropriate host is deemed to be within the scope of those skilled in the art from the teachings herein.

Preferably, the host cell genetically engineered is an animal cell, and most preferably CHO-S cell (INVITROGEN, cat No 11619-012).

Chinese hamster ovary (CHO) cells are frequently used in the biopharmaceutical industry for the manufacture of biologics such as recombinant proteins, antibodies, peptibodies, and receptor ligands. One of the reasons that CHO cells are often used is that these cells have an extensive safety track record for biologics production. This is considered to be a well-characterized cell line and, as a result, the safety testing required may be less rigorous in some respects (e.g., retroviral safety) than that required for other cell types. Nevertheless, the production of interleukin 15 is very difficult, especially in this cell.

The introduction of the nucleic acid or of the vector described previously into the host cell can be done by methods well known from one of skill in the art such as calcium phosphate transfection; DEAE-Dextran mediated transfection, or electroporation.

The present invention also relates to a method of producing a host cell genetically engineered expressing an immunocytokine according to the invention, said method comprising the steps of: (i) introducing in vitro or ex vivo a nucleic acid or a vector as described above into a host cell, (ii) culturing in vitro or ex vivo the recombinant host cell genetically engineered obtained and (iii), optionally, selecting the cells which express and/or secrete said immunocytokine. Such recombinant host cells can be used for the production of immunocytokine of the invention.

Pharmaceutical Composition Comprising the Immunocytokine of the Invention

A further object of the invention relates to a pharmaceutical composition comprising the immunocytokine as described above, a nucleic acid encoding thereof, or a vector comprising said nucleic acid, eventually associated with a pharmaceutically acceptable carrier.

The expression "pharmaceutically acceptable" refers to molecular entities and compositions that are physiologically tolerable and do not typically produce allergic or similar undesirable reactions, such as gastric upset, dizziness and the like when administered to a human. Preferably, as used herein, the expression "pharmaceutically acceptable" means approvable by a regulatory agency of the Federal or state government or listed in the U.S. Pharmacopeia or other generally recognized pharmacopeia for use in animals, and more particularly in humans.

The term "carrier" refers to a solvent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like.

The pharmaceutical composition comprises an "effective amount" of the immunocytokine of the invention, which effective amount is sufficient to inhibit the growth of cancer cells, preferably sufficient to induce the regression of tumor growth. The doses used for the administration can be adapted as a function of various parameters, in particular as a function of the mode of administration used, of the relevant pathology, or alternatively of the desired duration of treatment. Naturally, the form of the pharmaceutical composition, the route of administration, the dosage and the regimen naturally depend on the condition to be treated, the severity of the illness, the age, weight, and sex of the subject, etc. The ranges of effective doses provided below are not intended to limit the invention and represent preferred dose ranges. However, the preferred dose can be tailored to the individual subject, as is understood and determinable by one of skill in the art, without undue experimentation.

In view of the marked efficiency of the immunocytokine of the invention, the skilled person can plan to use very small doses for treating a subject. As a non limiting example, the immunocytokine of the invention can be can be administered by injection at a dose comprised between 50 mg/kg and 5 µg/kg of subject, preferably at a dose comprised between 10 mg/kg and 100 µg/kg and most preferably at a dose comprised between of 2.5 mg/kg and 500 µg/kg.

As an example, the pharmaceutical compositions of the invention can be formulated for topical, oral, intranasal, intraocular, intravenous, intramuscular, intratumoral or subcutaneous administrations and the like. Preferably, the pharmaceutical composition contains vehicles which are pharmaceutically acceptable for a formulation intended to be injected. These may be in particular isotonic, sterile, saline solutions (monosodium or disodium phosphate, sodium, potassium, calcium or magnesium chloride and the like or mixtures of such salts), or dry, especially freeze-dried compositions which upon addition, depending on the case, of sterilized water or physiological saline, permit the constitution of injectable solutions. Suitable pharmaceutical carriers are described in "Remington's Pharmaceutical Sciences" by E. W. Martin.

The immunocytokine of the invention, nucleic acids coding therefore or nucleic acid vectors may be solubilized in a buffer or water or incorporated in emulsions, microemulsions, hydrogels (e.g. PLGA-PEG-PLGA triblock copolymers-based hydrogels), in microspheres, in nanospheres, in microparticles, in nanoparticles (e.g. poly(lactic-co-glycolic acid) microparticles (e.g. poly lactic acid (PLA); poly (lactide-co-glycolic acid) (PLGA); polyglutamate microspheres, nanospheres, microparticles or nanoparticles), in liposomes, or other galenic formulations. In all cases, the formulation must be sterile and fluid to the extent of acceptable syringability. It must be stable under the conditions of manufacture and storage and must be preserved against the contaminating action of microorganisms, such as bacteria and fungi.

Solutions of the active compounds as free base or pharmacologically acceptable salts can be prepared in water suitably mixed with a surfactant, such as hydroxypropylcellulose.

Dispersions can also be prepared in glycerol, liquid polyethylene glycols, and mixtures thereof and in oils. Under ordinary conditions of storage and use, these preparations contain a preservative to prevent the growth of microorganisms.

The immunocytokines according to the invention can be formulated into a composition in a neutral or salt form. Pharmaceutically acceptable salts include the acid addition salts (formed with the free amino groups of the protein) which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The carrier can also be a solvent or a dispersion medium containing, for example, water, ethanol, polyol (for example, glycerol, propylene glycol, and liquid polyethylene glycol, and the like), suitable mixtures thereof, and vegetables oils. The immunocytokines of the invention may also be modified, by pegylation as an example, so as to increase its biodisponibility. When the immunocytokine of the invention has a nucleic acid form, the carrier can also be a vector, such as a virus (e.g. MVA, rAAV, lentivirus, etc.)

The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride.

Prolonged absorption of the injectable compositions can be brought about by the use in the compositions of agents delaying absorption, for example, aluminium monostearate, gelatin, polyols, and half-life enhancing covalent and non covalent formulations.

There are numerous causes of peptide instability or degradation, including hydrolysis and denaturation. Hydrophobic interaction may cause clumping of molecules together (i.e. aggregation). Stabilizers may be added to reduce or prevent such problems.

Stabilizers include cyclodextrine and derivatives thereof (see U.S. Pat. No. 5,730,969). Suitable preservatives such as sucrose, mannitol, sorbitol, trehalose, dextran and glycerin can also be added to stabilize the final formulation. A stabilizer selected from ionic and non-ionic surfactants, D-glucose, D-galactose, D-xylose, D-galacturonic acid, trehalose, dextrans, hydroxyethyl starches, and mixtures thereof may be added to the formulation. Addition of alkali metal salt or magnesium chloride may stabilize a peptide. The peptide may also be stabilized by contacting it with a saccharide selected from the group consisting of dextran, chondroitin sulphuric acid, starch, glycogen, dextrin, and alginic acid salt. Other sugars that can be added include monosaccharides, disaccharides, sugar alcohols, and mixtures thereof (E.g., glucose, mannose, galactose, fructose, sucrose, maltose, lactose, mannitol, xylitol). Polyols may stabilize a peptide, and are water-miscible or water-soluble. Suitable polyols may be polyhydroxy alcohols, monosaccharides and disaccharides including mannitol, glycerol, ethylene glycol, propylene glycol, trimethyl glycol, vinyl pyrrolidone, glucose, fructose, arabinose, mannose, maltose, sucrose, and polymers thereof. Various excipients may also stabilize peptides, including serum albumin, amino acids, heparin, fatty acids and phospholipids, surfactants, metals, polyols, reducing agents, metal chelating agents, polyvinyl pyrrolidone, hydrolysed gelatin, and ammonium sulfate.

The promise of cytokine therapy does indeed derive from the identification of these novel cytokines but even more fundamentally, the field is greatly benefiting from the ever-expanding amount of preclinical data that convincingly demonstrate synergistic and/or novel biologic effects, which may be achieved through the use of several combinations of cytokines with complementary immune-stimulating capabilities. Potential therapeutic active agent combinations with RLI-based immunocytokines includes by example chemotherapeutic agents, antiangiogenic agents, or immunomodulatory agents.

In a preferred embodiment, the composition of the invention may comprise a further therapeutic active agent, such as chemotherapeutic agents, antiangiogenic agents, or immunomodulatory agents.

For chemotherapeutic agents, it has been demonstrated that their therapeutic effects could be mediated in part by an indirect effect on immune responses, either by inducing an immunogenic cell death, balancing the immunosuppressive environments, debulking the primary large tumor and then facilitating the immune attack or by inducing a transient lymphopenia followed by homeostatic lymphoproliferation. Many of them are well known from the skilled person and, and as an example of chemotherapeutic agent which can be combined with the immunocytokine of the invention, on can cite fludarabine, gemcitabine, capecitabine, methotrexate, taxol, taxotere, mercaptopurine, thioguanine, hydroxyurea, cytarabine, cyclophosphamide, ifosfamide, nitrosoureas, platinum complexes such as cisplatin, carboplatin and oxaliplatin, mitomycin, dacarbazine, procarbizine, etoposide, teniposide, campathecins, bleomycin, doxorubicin, idarubicin, daunorubicin, dactinomycin, plicamycin, mitoxantrone, L-asparaginase, doxorubicin, epimbicm, 5-fluorouracil, taxanes such as docetaxel and paclitaxel, leucovorin, levamisole, irinotecan, estramustine, etoposide, nitrogen mustards, BCNU, nitrosoureas such as carmustme and lomustine, vinca alkaloids such as vinblastine, vincristine and vinorelbine, imatimb mesylate, hexamethyhnelamine, topotecan, kinase inhibitors, phosphatase inhibitors, ATPase inhibitors, tyrphostins, protease inhibitors, inhibitors herbimycm A, genistein, erbstatin, and lavendustin A.

For antiangiogenic agents, it has been demonstrated that they have off-target effects on immune system and then could facilitate the tumor immune responses. As an example of antiangiogenic agent which can be combined with the immunocytokine of the invention, on can cite drugs targeting the vascular endothelial growth factor receptor (VEGFR) via its tyrosine kinase, such as sorafenib, sunitinib, and pazopanib, or the mammalian target of rapamycin (mTOR), such as temsirolimus and everolimus.

For immunomodulatory agents which can be combined with the immunocytokine of the invention, one can cite cytokines (IL-2, IL-7, IL-15, IL-12, IL18, IL-21, GM-CSF, G-CSF, IFNα, . . . ), chemokines/antiangiogenic cytokines (IP10, Mig, SDF-1, RANTES, . . . ), TLR agonists, and immunoregulatory antibodies (anti-CTLA4, anti-PD1, anti-TGFb, agonist anti-CD40, . . . ).

Therapeutic Methods and Uses

In a further aspect, the present invention relates to a pharmaceutical composition as described previously for treating cancer in a subject, preferably of a pharmaceutical composition comprising an immunocytokine as described previously.

As used herein, the term "subject" denotes a mammal, such as a rodent, a feline, a canine or a primate, and most preferably a human.

In another aspect, the present invention relates to products containing:

(i) an immunocytokine as describe above, a nucleic acid sequence coding therefore, or a vector comprising such a nucleic acid sequence, and (ii) a therapeutic agent, preferably an anticancer agent, as a combined preparation for simultaneous, separate, or sequential use for treating cancer in a subject.

In still another aspect, the present invention relates to a method for treating cancer in a subject comprising the step of administrating to said subject a pharmaceutical composition as described previously.

In a final aspect, the present invention relates to a method for treating cancer comprising the step of simultaneously, separately, or sequentially administrating to a subject in need thereof of a therapeutically effective amount of:

(i) an immunocytokine as describe above, a nucleic acid sequence coding therefore, or a vector comprising such a nucleic acid sequence, and (ii) a therapeutic agent, preferably an anticancer agent.

In the context of the invention, the term "treating" or "treatment", as used herein, means reversing, alleviating, inhibiting the progress of, or preventing the disorder or condition to which such term applies, or one or more symptoms of such disorder or condition. The expression "treating cancer" as used herein means the inhibition of the growth of cancer cells. Preferably such treatment also leads to the regression of tumor growth, i.e., the decrease in size of a measurable tumor. Most preferably, such treatment leads to the complete regression of the tumor.

Preferably said cancer is a carcinoma or a lung cancer.

Most preferably, the expression "treating cancer" means "treating cancer by activating Tumor-infiltrated Lymphocytes".

Accordingly, the cancer corresponds preferably to a vascularized cancer.

Still preferably, said cancer is a cancer with an anergic TIL population, said cancer corresponding to advanced cancer such as Renal Cell Carcinoma (RCC).

In the following, the invention is described in more detail with reference to amino acid sequences, nucleic acid sequences and examples. However, no limitation of the invention is intended by the details of the examples. Rather, the invention pertains to any embodiment which comprises details which are not explicitly mentioned in the examples herein, but which the skilled person finds without undue effort.

EXAMPLES 1) of RLI-Based Modulokines

Construction of Anti-PD-1 (hBAT) RLI Immunocytokines

An expression plasmid encoding for the anti-PD-1 light chain (corresponding to the one of CT-01 1 (hBAT or hBAT-1). The chimeric IgG heavy chain sequences of the antibody were designed to be fused in 3'term with or without a linker of 22 amino-acid (SEQ ID no. 16) to IL15 (SEQ ID no. 3, wherein the amino acid at position 93 is K). These nucleotide sequences were synthesized and cloned in pcDNA3.1 plasmids by GENEART. The complete sequence of light and heavy chains of the anti-PD-1 antibody are disclosed in the international patent application WO2009/101611.

Plasmid DNA Preparation and Transfection Reagent

A 40 kDa linear PEI was obtained from POLYSCIENCE. A 1 mg/mL stock solution was prepared by dissolving the PEI in water with heating, neutralizing by NaOH, and sterilizing by filtration through a 0.22 μm filter. The solution stock was aliquoted and stored at −20° C.

Plasmids DNA for transfections were purified using the plasmid purification kits following the manufacturer's protocol (MACHEREY-NAGEL) and sterilizing by filtration through a 0.22 μm filter.

Production and Purification of the Immunocytokines

1-Transient Transfection in Suspension:

Routinely maintained CHO-S (INVITROGEN) cells were seeded at a density of $1 \times 10^6$ cells/mL in PowerCHO2 Medium (LONZA) and cultured overnight at 37° C. in a shaking incubator (100 rpm) with 5% $CO_2$. For transfection, cells were then diluted to $2 \times 10^6$ cells/mL in. CD-CHO medium (INVITROGEN). The transfection complexes were prepared in 10% of the culture volume using NaCl 150 mM. Expression constructs DNA (2.5 mg/L of culture volume, using a 1:2 ration of plasmid encoding heavy chain to plasmid encoding light chain) were mixed with PEI diluted in NaCl (10 mg/L of final culture volume) and incubated for 10 min at room temperature before adding to the culture. Cells were cultured in a shaking incubator (130 rpm) at 37° C. for 5 h before doubling the culture volume with PowerCHO2 medium. Supernatant were collected 5 days postransfection.

2-Stable Transfection on Adherent Cells

CHO-K1 cells (ATCC no CCL-61) were grown in DMEM supplemented with 1-glutamine, 10% FCS and penicillin (100 units/ml)/streptomycin (100 μg/ml) and transfected with each vector using lipofectamine 2000 reagent (INVITROGEN), as recommended by the manufacturer. Clones were selected by limit dilution with medium containing geneticin and hygromycin (0.5 mg/ml) or blasticin and hygromycin (5 μg/mL and 100 μg/mL) for the anti-GD2O-aceylated ICK and anti-CD20 ICK, respectively. Culture supernatant of each clone was assayed for bifunctional proteins production by ELISA. For the production of ICK, selected clones were amplified in 25% DMEM medium and 75% AIM medium (INVITROGEN). Cells were then maintained in 100% of AIM, and supernatant were collected and replaced every 2 days, for 10 days.

3-Supernatant Purification:

Collected supernatant were centrifuged at 3000 rpm for 20 minutes at 4° C., equilibrated at pH 7.8 with NaOH and filtered through a 0.22 μm filter. The conditioned mediums were purified by affinity chromatography using a protein A column (GE) according to the manufacturer's instructions. The purified proteins were concentrated with a 50 kDa AMICON units (MILLIPORE). During this step, elution buffer was replaced by PBS. The Purified proteins were finally assayed by ELISA and absorbance measuring at 280 nm. Purity was evaluated by electrophoresis.

4-Detection of the Immunoglobulin Moiety by ELISA.

Maxisorp flat bottom microtiter plate (NUNC) was coated with 100 μL of goat anti-human antibody (UP892370, INTERCHIM) diluted in PBS to 1.5 μg/mL for h at 4° C. Plate was then blocked with 200 μL of blocking buffer (1% BSA+0.1% TWEEN 20 in PBS) for 1 h at 37° C. Plate was then washed 3 times with washing buffer (0.1% TWEEN 20 in PBS) and sample diluted in blocking buffer were added and incubated 30 min at 37° C. (100 μL). After 3 washing, Peroxidase conjugated goat anti-human IgG1 (109-036-003, JACKSON) diluted 1:10000 was added and incubated for 30 min at 37° C. TMB substrate (INTERCHIM) was used to determine protein levels and plates were read at 450 nm. Purified Rituximab (ROCHE) was used to generate a standard curve on plate.

5-Detection of the Cytokine Moiety by ELISA.

Maxisorp flat bottom microtiter plate (NUNC) was coated with 100 μL of the anti-IL15 B-E29 (DIACLONE) diluted in carbonate buffer to 2 μg/mL for 16 h at 4° C. Plate was then blocked with 200 μL of blocking buffer (1% BSA in PBS) for 1 h at 37° C. the plate was then washed 3 times with washing buffer (0.05% Tween 20 in PBS). Sample diluted in TBS+0,05% BSA were added and incubated 1h30 min at 37° C. (100 μL). After 3 washing, biotinylated anti-IL15 antibody BAM 247 (R&D SYSTEM) diluted to 200 ng/mL was added and incubated for 1h30 min at 37° C. The plate was washed 3 times and peroxidase conjugated streptavidin was added dilution 1:1000. TMB substrate (INTERCHIM) was used to determine protein levels and plates were read at 450 nm. IL-15 (PEPROTECH) was used to generate a standard curve on plate.

Phenotypes of TILs

Tumor infiltrated lymphocytes (TILs) were obtained from biopsies or nephrectomie tissues derived from 2 renal cell carcinoma patients after DNAse and collagenase digestion. These TILs were mostly anergic enabling tumor progression.

The phenotype of these TILs in relation to PD-1, Tim-3 and IL-15Rα was determined by immunofluorescence.

The FIG. 1 shows the obtained phenotype for patient A (FIG. 1A) and for patient B (FIG. 1B).

Binding Activity of the Immunocytokines

The specific binding of the anti-PD-1 RLI modulokine was assessed by flow cytometry. The capacity of modulokine to bind IL-15 receptor on effector cells were tested on Kit225. modulokine coated on targeted cells were revealed with a PE-conjugated goat anti-human IgG mAb (PN IM0550, BECKMAN COULTER), or with a biotinylated mouse anti-IL15 antibody (BAM247, R&D SYSTEM) coupled to PE-streptavidin (SIGMA-ALDRICH). Targeted cells ($1 \times 10^5$) were incubated with each ICK for 1 h at 4° C., washed and then incubated with a PE-conjugate for 1 h at 4° C. Washed cells were finally analyzed on a FACSCALIBUR (BECTON DICKINSON).

The results have shown that the modulokine bind to the IL-15 receptor and also to PD-1.

Proliferation Activity of the Immunocytokines

The interleukin-15 mediated proliferation activity of the obtained modulokine was tested and compared to RLI. The proliferative responses of Kit 225 and 32Dβ cells to ICK were measured by [$^3$H] thymidine incorporation. Cells were maintained in culture medium for 3 days, washed twice, and starved in medium without cytokine for 24 h or 4 h for Kit 225 and 32Dβ, respectively. They were then seeded in multiwell plates at $10^4$ cells/well in 100 μl and cultured for 48 h in medium supplemented with increasing concentration of sample. Human rIL-15 and RLI were used as calibrator. Cells were pulsed for 16 h with 0.5 μCi/well of [$^3$H] thymidine, harvested onto glass fiber filters, and cell-associated radioactivity was measured. The results have confirmed that the proliferation activity of the modulokine was comparable to the one of RLI Strong TILs Reactivation by the RLI Modulokine Tumor infiltrated lymphocytes (TILs) were obtained from biopsies or nephrectomie tissues derived from 25 renal cell carcinoma patients after DNAse and collagenase digestion. These TILs were mostly anergic enabling tumor progression.

The TILs reactivation from the 25 patients was tested by incubating said TILs in the absence or in the presence of the same molarity for each patient of RLI, HBAT (CT011=anti-PD1 antibody), HBAT-RLI (modulokine), or the combination of HBAT and RLL RLI was used at 1 μg/ml for patients 1-8 and then at 300 ng/ml for patients 9-25.

The supernatants were collected 48 hours after stimulation and the reactivation was determined by measuring by ELISA the concentration of IFNγ in the supernatant.

The raw data from the 25 TIL derived from renal cell carcinoma patients are presented in table 1, except for the unstimulated TILs, which always secreted less than 20 pg/ml of IFNγ.

Combinaison

TABLE 1

| Patient | pg/ml of IFNγ. | | | |
|---|---|---|---|---|
| | RLI | HBAT | HBAT − RLI | HBAT + RLI |
| 1 | 440 | 0 | 1070 | ND |
| 2 | 267 | 0 | 338 | ND |
| 3 | 365 | 28 | 2000 | 377 |
| 4 | 150 | 92 | 2280 | 1500 |
| 5 | 290 | ND | 7700 | 2900 |
| 6 | 570 | 80 | 970 | 700 |
| 7 | 0 | 0 | 0 | 0 |
| 8 | 15 | 15 | 32 | 25 |
| 9 | 320 | 17 | 1570 | 360 |
| 10 | 245 | 0 | 635 | 245 |
| 11 | 260 | 320 | 2000 | 1490 |
| 12 | 310 | 22 | 1100 | 360 |
| 13 | 170 | 160 | 3600 | 1800 |
| 14 | 0 | 9 | 50 | 0 |
| 15 | 840 | 27 | 2500 | 1000 |
| 16 | 15 | 73 | 0 | 50 |
| 17 | 0 | 0 | 0 | 0 |
| 18 | 125 | 55 | 800 | 230 |
| 19 | 170 | 0 | 4500 | 0 |
| 20 | 0 | 33 | 330 | 0 |
| 21 | 80 | 0 | 395 | 0 |
| 22 | 125 | 65 | 1500 | 1000 |
| 23 | 0 | 0 | 0 | 0 |
| 24 | 30 | 65 | 2500 | 540 |
| 25 | 390 | ND | 3600 | ND |

Figure 2:
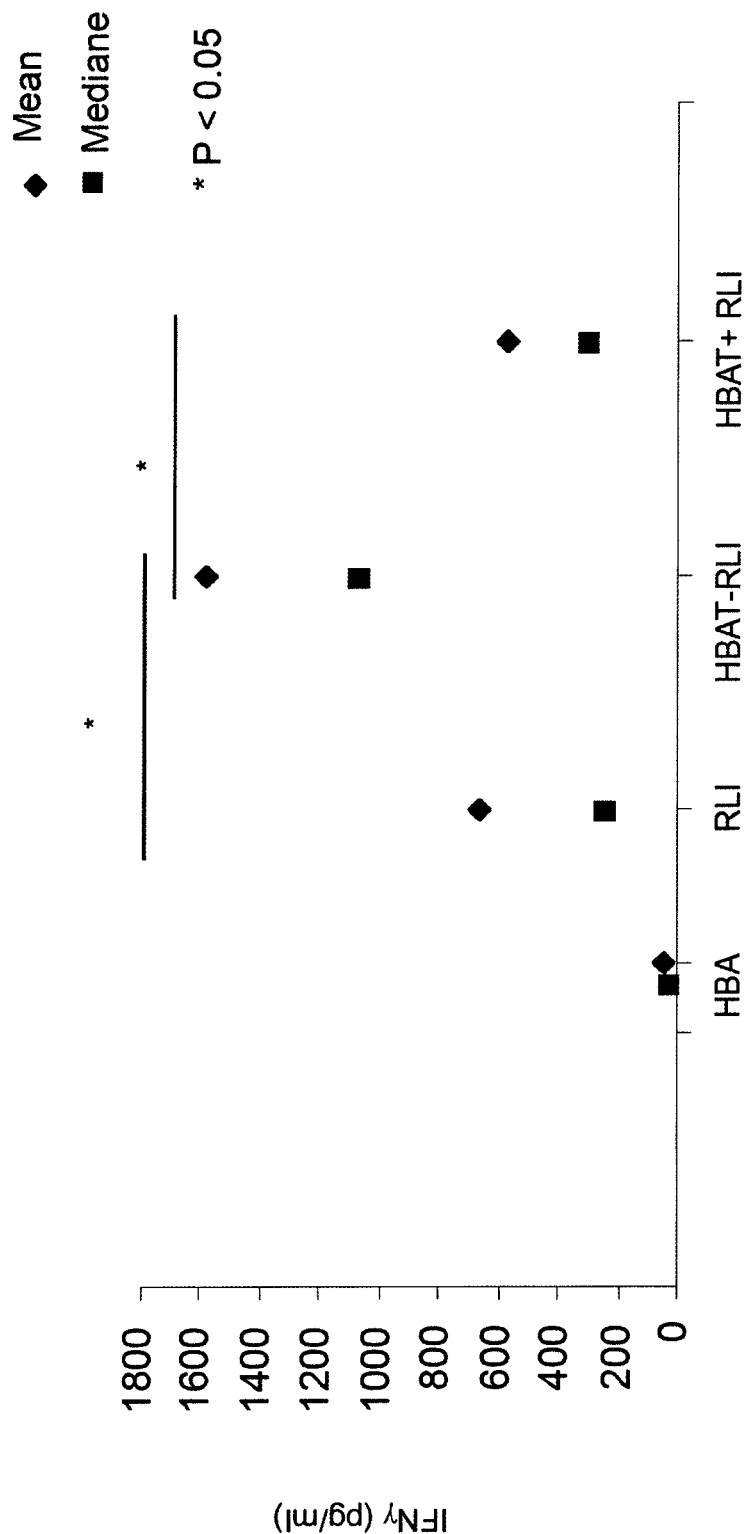
FIG. 2 shows the reactivation of Tumor infiltrated lymphocytes (TILs) induced by anti-PD1 antibody (HBAT), by RLI, by a combination of RLI and HBAT (RLI+HBAT) or by the modulokine of the invention (HBAT–RLI).

The FIG. 2 shows the Mean and Median of IFNγ produced from TIL activated with RLI, HBAT, HBAT-RLI and HBAT+RLI (* p<0.05).

The results show that nearly no TILs activation was obtained with the anti-PD-1 antibody alone. Some TIL activation was obtained with RLI alone or combined with the anti-PD1 antibody. Now, and surprisingly, a strong and general activation as compared to RLI and also RLI+HBAT was obtained with the immunocytokine of the invention (table 1 and FIG. 2).

These results enable to envisage new therapies.

Evaluation of the Efficacy of the Modulokine in the Carcinoma CT26 Experimental Tumor Model CT26 is an n-nitroso-n-methylurethane-(nnmu) induced, undifferentiated colon mouse carcinoma cell line.

BALB/C mice will be injected subcutaneously on the right flank with CT26 tumor cells ($2 \cdot 10^5$/mouse).

On day 9, when tumours should reach 20-30 mm², different groups of mice are treated with 16 or 32 μg/mouse of the modulokine anti-PD1-RLI alone in comparison to equimolar concentrations of the anti-PD1 alone, the RLI alone (1004-14p), the combination between anti-PD1 and RLI or PBS in the control group.

The modulokine or RLI alone are injected from day 9 twice a week for 4 weeks. The anti-PD1 antibody alone is injected from day 9 and then once a week for 4 weeks. In the combination group, the anti-PD1 antibody is injected from day 9 and then once a week for 4 weeks and RLI from day 15 and then twice a week for 3 weeks. Tumors is measured three times per week with a calliper and tumor area was calculated as follow: length×width. Mice are sacrificed when tumour size reached 300 mm² or were ulcerated. Primary tumor growth, survival and eventually regression will be assessed. Control groups received a corresponding dose of antibody isotype or irrelevant RLI-antibody conjugate (anti-HER2-RLI).

BALB/C mice were injected subcutaneously on the right flank with CT26 tumor cells ($2 \cdot 10^5$/mouse). On day 9, when tumours reached 20-30 mm² mice were treated i.p. with 16 or 32 μg/mouse of the modulokine anti-PD-L1-RLI alone in comparison to equimolar concentrations of the anti-PD-L1 (clone 10 F.9G2, BIO-XCELL) alone, the RLI alone (1004-14p), the combination between anti-PD-L1 (clone 10 F.9G2, BIO-XCELL) and RLI or PBS in the control group.

The modulokine or RLI alone are injected from day 9 twice a week for 4 weeks. The anti-PD1 antibody alone is injected from day 9 and then once a week for 4 weeks. In the combination group, the anti-PD1 antibody is injected from day 9 and then once a week for 4 weeks and RLI from day 15 and then twice a week for 3 weeks. Tumors is measured three times per week with a calliper and tumor area was calculated as follow: length×width. Mice are sacrificed when tumour size reached 300 mm² or were ulcerated. Primary tumor growth, survival and eventually regression will be assessed. Control groups received a corresponding dose of antibody isotype or irrelevant RLI-antibody conjugate (anti-HER2-RLI).

Evaluation of the Efficacy of the Modulokine in the Lung tc-1 Experimental Tumor Model The tumor cell line, TC-1 was derived from primary lung epithelial cells of C57Bl/6 mice. The cells were immortalized with the amphotropic retrovirus vector lxsn16e6e7 and subsequently transformed with the pvejb plasmid expressing the activated human c-ha-ras oncogene. The cells are positive for the expression of HPV-16 E7.

C57Bl/6 mice will be injected subcutaneously on the right flank with TC-1 tumor cells ($1 \cdot 10^5$/mouse). On day 9, when tumours should reach 20-50 mm², different groups of mice are treated with 16 or 32 μg/mouse, of the modulokine anti-PD1-RLI alone in comparison to equimolar concentrations of the anti-PD1 alone, the RLI alone (1004-14p), the combination between anti-PD1 and RLI or PBS in the control group. The modulokine or RLI alone is injected from day 9 twice a week for 4 weeks. The anti-PD1 antibody alone is injected from day 9 and then once a week for 4 weeks. In the combination group, the anti-PD1 antibody is injected from day 9 and then once a week for 4 weeks and RLI from day 15 and then twice a week for 3 weeks. Tumors are measured three times per week with a calliper and tumor area was calculated as follow: length×width. Mice are sacrificed when tumour size reached 300 mm² or are ulcerated. Primary tumor growth, survival and eventually regression are assessed.

Evaluation of the Efficacy of the Modulokine in the Metastatic Melanoma B16F10 Experimental Tumor Model B16F10 tumors are implanted by injection of $3 \times 10^4$ B16F10 cells in the flank of C57BL/6 mice, i.d. at day 0. After allowing the tumor cells to engraft, therapy is initiated on day 4. The anti-PD-L1-RLI modulokine is injected i.p. at 16 or 32 μg/mouse in comparison to equimolar concentrations of the anti-PD-L1 alone (clone 10 F.9G2, BIO-XCELL), the RLI alone (1004-14p), the combination between anti-PD-L1 ((clone 10 F.9G2, BIO-XCELL)) and RLI or PBS in the control group.

The modulokine, the anti-PD-L1 mAb, RLI or the combination of anti-PD-L1 mAb+RLI are injected from day 4 twice a week for 4 weeks. Tumors is measured three times per week with a calliper and tumor area was calculated as follow: length×width. Mice are sacrificed when tumor size reached 300 mm² or were ulcerated. Primary tumor growth, survival and eventually regression will be assessed. Control groups received a corresponding dose of antibody isotype or irrelevant RLI-antibody conjugate (anti-HER2-RLI).

Evaluation of the Efficacy of the Modulokine in the Advanced Bladder Cancer MB49 Experimental Tumor Model The MB49 tumour cell line originates from a carcinogen-induced tumour of bladder epithelial origin from C57BL/6 male mice. $10^6$ MB49 bladder cancer cells were injected s.c. into the upper dermis in the back of C57BL/6 mice. Treatment is initiated on day 6 after tumor inoculation which corresponds to when tumors become clearly visible and palpable at a size of ≈15 mm2. The anti-PD-1-RLI and anti-PD-L1 modulokines are injected i.p. at 16 or 32 µg/mouse in comparison to equimolar concentrations of the anti-PD1 alone, the anti-PD-L1 alone (clone 10 F.9G2, BIO-XCELL), the RLI alone (1004-14p), the combination between anti-PD1 or anti-PD-L1 (clone 10 F.9G2, BIO-XCELL) with RLI or PBS in the control group.

The modulokines, the anti-PD-1 mAb, the anti-PD-L1 mAb (clone 10 F.9G2, BIO-XCELL), RLI and the combination of anti-PD-1 mAb or anti-PD-L1 (clone 10 F.9G2, BIO-XCELL)+RLI are injected from day 6 twice a week for 4 weeks. Tumors are measured three times per week with a calliper and tumor area was calculated as follow: length×width. Mice are sacrificed when tumour size reached 300 mm² or were ulcerated. Primary tumor growth, survival and eventually regression will be assessed. Control groups received a corresponding dose of antibody isotype or irrelevant RLI-antibody conjugate (anti-HER2-RLI).

Evaluation of the Efficacy of the Modulokine in the Breast Cancer 4T1 Experimental Tumor Model BALB/c mice were inoculated with $5 \times 10^4$ 4 T1 breast cancer cells in the mammary gland on day 0. Treatment is initiated on day 10 after tumor inoculation which corresponds to when tumors become clearly visible and palpable at a size of ≈15-20 mm2. The anti-PD-1-RLI and anti-PD-L1 modulokines are injected i.p. at 16 or 32 µg/mouse in comparison to equimolar concentrations of the anti-PD1 alone, the anti-PD-L1 alone (clone 10 F.9G2, BIO-XCELL), the RLI alone (1004-14p), the combination between anti-PD1 or anti-PD-L1 (clone 10 F.9G2, BIO-XCELL) with RLI or PBS in the control group.

The modulokines, the anti-PD-1 mAb, the anti-PD-L1 mAb (clone 10 F.9G2, BIO-XCELL), RLI and the combination of anti-PD-1 mAb or anti-PD-L1 (clone 10 F.9G2, BIO-XCELL)+RLI are injected from day 10 twice a week for 4 weeks. Control groups received a corresponding dose of antibody isotype or irrelevant RLI-antibody conjugate (anti-HER2-RLI). Tumors are measured three times per week with a calliper and tumor area was calculated as follow: length×width. Mice were sacrificed at day 27. Lung metastatic nodules are counted under a binocular microscope.

Evaluation of the Efficacy of the Modulokine in the Ovary Cancer 1D8 Experimental Tumor Model ID8-VEGF ovarian carcinoma cell line was developed previously from a mouse ovarian epithelial papillary serous adenocarcinoma cell line. C57BL/6 mice were implanted subcutaneously on the right flank with either $5 \times 10^6$ ID8 tumor cells. Treatment is initiated on day 10 after tumor inoculation which corresponds to when tumors become clearly visible and palpable at a size of ≈15-20 mm2. The anti-PD-1-RLI and anti-PD-L1 modulokines are injected i.p. at 16 or 32 µg/mouse in comparison to equimolar concentrations of the anti-PD1 alone, the anti-PD-L1 alone (clone 10 F.9G2, BIO-XCELL), the RLI alone (1004-14p), the combination between anti-PD1 or anti-PD-L1 (clone 10 F.9G2, BIO-XCELL) with RLI or PBS in the control group.

The modulokines, the anti-PD-1 mAb, the anti-PD-L1 mAb (clone 10 F.9G2, BIO-XCELL), RLI and the combination of anti-PD-1 mAb or anti-PD-L1 (clone 10 F.9G2, BIO-XCELL)+RLI are injected from day 10 twice a week for 4 weeks. Control groups received a corresponding dose of antibody isotype or irrelevant RLI-antibody conjugate (anti-HER2-RLI). Tumors were measured three times per weeks with a calliper and tumor area was calculated as follow: length×width. Mice were sacrificed when tumour size reached 300 mm² or were ulcerated.

Evaluation of the Efficacy of the Modulokine in the Prostate Cancer RM-1 Experimental Tumor Model C57BL/6 female mice are inoculated s.c. with $2 \times 10^5$ RM-1 murine prostate cancer cells. Treatment is initiated on day 3 after tumor inoculation which corresponds to when tumors become clearly visible and palpable at a size of ≈15-20 mm2. The anti-PD-1-RLI and anti-PD-L1 modulokines are injected i.p. at 16 or 32 µg/mouse in comparison to equimolar concentrations of the anti-PD1 alone, the anti-PD-L1 alone (clone 10 F.9G2, BIO-XCELL), the RLI alone (1004-14p), the combination between anti-PD1 or anti-PD-L1 (clone 10 F.9G2, BIO-XCELL) with RLI or PBS in the control group.

The modulokines, the anti-PD-1 mAb, the anti-PD-L1 mAb (clone 10 F.9G2, BIO-XCELL), RLI and the combination of anti-PD-1 mAb or anti-PD-L1 (clone 10 F.9G2, BIO-XCELL)+RLI are injected from day 3 twice a week for 4 weeks. Control groups received a corresponding dose of antibody isotype or irrelevant RLI-antibody conjugate (anti-HER2-RLI). Tumors were measured three times per weeks with a calliper and tumor area was calculated as follow: length×width. Mice were sacrificed when tumour size reached 300 mm² or were ulcerated.

We claim:

1. An immunocytokine comprising of:
   a polypeptide conjugate and an immunomodulatory antibody or an antigen binding fragment thereof, which are covalently linked as a fusion protein,
   wherein said immunomodulatory antibody or antigen binding fragment thereof binds to a PD-1 receptor; and
   wherein said polypeptide conjugate comprises:
   (i) an interleukin 15 comprising a) the amino acid sequence of SEQ ID NO: 3, or b) a variant thereof of a) comprising at least one amino acid substitution selected from L45D, L45E, S51D, L52D, N72D, N72E, N72A, N72S, N72Y and N72P according to SEQ ID NO: 3, wherein the variant has the IL-15 activity;
   (ii) an IL-15Rα fragment comprising the sushi domain and the hinge domain of an IL-15Ra, and comprising the amino acid sequence of SEQ ID NO: 12; and
   (iii) a flexible peptide linker joining the IL-15Ra fragment and the IL-15 to form a fusion protein.

2. The immunocytokine of claim 1, comprising, from N- to C-terminal, the immunomodulatory antibody or antigen binding fragment thereof, the IL-15Ra fragment, and the IL-15.

3. The immunocytokine of claim 1, wherein the linker consists of 18-22 amino acids.

4. The immunocytokine of claim 1, wherein the linker consists of 20 amino acids.

5. The immunocytokine of claim 1, wherein the linker consists of the amino acid sequence of SEQ ID NO: 13, SEQ ID NO: 14 or SEQ ID NO: 15.

6. The immunocytokine of claim 1, wherein the polypeptide conjugate comprises the amino acid sequence of SEQ ID NO:18 or SEQ ID NO: 19.

7. A pharmaceutical composition comprising the immunocytokine of claim 1 and a pharmaceutically acceptable carrier.

* * * * *

SEQUENCE LISTING

```
<160> NUMBER OF SEQ ID NOS: 19

<210> SEQ ID NO 1
<211> LENGTH: 114
<212> TYPE: PRT
<213> ORGANISM: artificial sequence
<220> FEATURE:
<223> OTHER INFORMATION: mammalian interleukin 15 consensus sequence
<220> FEATURE:
<221> NAME/KEY: MISC_FEATURE
<222> LOCATION: (1)..(1)
```

```
<223> OTHER INFORMATION: X= N, S, T or I
<220> FEATURE:
<221> NAME/KEY: MISC_FEATURE
<222> LOCATION: (3)..(3)
<223> OTHER INFORMATION: X= V, H, I, Q or E
<220> FEATURE:
<221> NAME/KEY: MISC_FEATURE
<222> LOCATION: (4)..(4)
<223> OTHER INFORMATION: X= N, Y, F or D
<220> FEATURE:
<221> NAME/KEY: MISC_FEATURE
<222> LOCATION: (6)..(6)
<223> OTHER INFORMATION: X= I or R
<220> FEATURE:
<221> NAME/KEY: MISC_FEATURE
<222> LOCATION: (7)..(7)
<223> OTHER INFORMATION: X= S, N, L, Y, K or R
<220> FEATURE:
<221> NAME/KEY: MISC_FEATURE
<222> LOCATION: (10)..(10)
<223> OTHER INFORMATION: X= K, E, R or Q
<220> FEATURE:
<221> NAME/KEY: MISC_FEATURE
<222> LOCATION: (11)..(11)
<223> OTHER INFORMATION: X= K, T or R
<220> FEATURE:
<221> NAME/KEY: MISC_FEATURE
<222> LOCATION: (13)..(13)
<223> OTHER INFORMATION: X= E, D or Q
<220> FEATURE:
<221> NAME/KEY: MISC_FEATURE
<222> LOCATION: (14)..(14)
<223> OTHER INFORMATION: X= D, H, S or N
<220> FEATURE:
<221> NAME/KEY: MISC_FEATURE
<222> LOCATION: (16)..(16)
<223> OTHER INFORMATION: X= I or T
<220> FEATURE:
<221> NAME/KEY: MISC_FEATURE
<222> LOCATION: (17)..(17)
<223> OTHER INFORMATION: X=Q, R or K
<220> FEATURE:
<221> NAME/KEY: MISC_FEATURE
<222> LOCATION: (18)..(18)
<223> OTHER INFORMATION: X= S or F
<220> FEATURE:
<221> NAME/KEY: MISC_FEATURE
<222> LOCATION: (19)..(19)
<223> OTHER INFORMATION: X= M, I or L
<220> FEATURE:
<221> NAME/KEY: MISC_FEATURE
<222> LOCATION: (21)..(21)
<223> OTHER INFORMATION: X= I, V or M
<220> FEATURE:
<221> NAME/KEY: MISC_FEATURE
<222> LOCATION: (23)..(23)
<223> OTHER INFORMATION: X=A or T
<220> FEATURE:
<221> NAME/KEY: MISC_FEATURE
<222> LOCATION: (28)..(28)
<223> OTHER INFORMATION: X=E or D
<220> FEATURE:
<221> NAME/KEY: MISC_FEATURE
<222> LOCATION: (30)..(30)
<223> OTHER INFORMATION: X= D or G
<220> FEATURE:
<221> NAME/KEY: MISC_FEATURE
<222> LOCATION: (31)..(31)
<223> OTHER INFORMATION: X= V, F, A or I
<220> FEATURE:
<221> NAME/KEY: MISC_FEATURE
<222> LOCATION: (34)..(34)
<223> OTHER INFORMATION: X= S, N or R
<220> FEATURE:
<221> NAME/KEY: MISC_FEATURE
<222> LOCATION: (37)..(37)
<223> OTHER INFORMATION: X= V or I
<220> FEATURE:
<221> NAME/KEY: MISC_FEATURE
```

```
<222> LOCATION: (39)..(39)
<223> OTHER INFORMATION: X= A or T
<220> FEATURE:
<221> NAME/KEY: MISC_FEATURE
<222> LOCATION: (41)..(41)
<223> OTHER INFORMATION: X= K, Q or N
<220> FEATURE:
<221> NAME/KEY: MISC_FEATURE
<222> LOCATION: (48)..(48)
<223> OTHER INFORMATION: X= Q, G, R, H or E
<220> FEATURE:
<221> NAME/KEY: MISC_FEATURE
<222> LOCATION: (51)..(51)
<223> OTHER INFORMATION: X= S or L
<220> FEATURE:
<221> NAME/KEY: MISC_FEATURE
<222> LOCATION: (52)..(52)
<223> OTHER INFORMATION: X= L, Q or H
<220> FEATURE:
<221> NAME/KEY: MISC_FEATURE
<222> LOCATION: (54)..(54)
<223> OTHER INFORMATION: X= S, F or Y
<220> FEATURE:
<221> NAME/KEY: MISC_FEATURE
<222> LOCATION: (55)..(55)
<223> OTHER INFORMATION: X= G, K, S, N or R
<220> FEATURE:
<221> NAME/KEY: MISC_FEATURE
<222> LOCATION: (56)..(56)
<223> OTHER INFORMATION: X= D, H, S or N
<220> FEATURE:
<221> NAME/KEY: MISC_FEATURE
<222> LOCATION: (57)..(57)
<223> OTHER INFORMATION: X= A, H, M, E, G, S or T
<220> FEATURE:
<221> NAME/KEY: MISC_FEATURE
<222> LOCATION: (58)..(58)
<223> OTHER INFORMATION: X= S, V, P, T, N or D
<220> FEATURE:
<221> NAME/KEY: MISC_FEATURE
<222> LOCATION: (59)..(59)
<223> OTHER INFORMATION: X= I or L
<220> FEATURE:
<221> NAME/KEY: MISC_FEATURE
<222> LOCATION: (60)..(60)
<223> OTHER INFORMATION: X=  H, S, K, N, Y or E
<220> FEATURE:
<221> NAME/KEY: MISC_FEATURE
<222> LOCATION: (61)..(61)
<223> OTHER INFORMATION: X=  D or E
<220> FEATURE:
<221> NAME/KEY: MISC_FEATURE
<222> LOCATION: (62)..(62)
<223> OTHER INFORMATION: X=  T, I or A
<220> FEATURE:
<221> NAME/KEY: MISC_FEATURE
<222> LOCATION: (63)..(63)
<223> OTHER INFORMATION: X=  V or I
<220> FEATURE:
<221> NAME/KEY: MISC_FEATURE
<222> LOCATION: (64)..(64)
<223> OTHER INFORMATION: X=  E, T, Q, R or K
<220> FEATURE:
<221> NAME/KEY: MISC_FEATURE
<222> LOCATION: (66)..(66)
<223> OTHER INFORMATION: X=  L or V
<220> FEATURE:
<221> NAME/KEY: MISC_FEATURE
<222> LOCATION: (67)..(67)
<223> OTHER INFORMATION: X= I, T or L
<220> FEATURE:
<221> NAME/KEY: MISC_FEATURE
<222> LOCATION: (68)..(68)
<223> OTHER INFORMATION: X=I, M, F, Y or L
<220> FEATURE:
<221> NAME/KEY: MISC_FEATURE
<222> LOCATION: (72)..(72)
<223> OTHER INFORMATION: X= N, T, R, D or S
<220> FEATURE:
```

```
<221> NAME/KEY: MISC_FEATURE
<222> LOCATION: (73)..(73)
<223> OTHER INFORMATION: X= S, N, R, T or I
<220> FEATURE:
<221> NAME/KEY: MISC_FEATURE
<222> LOCATION: (75)..(75)
<223> OTHER INFORMATION: X= S or N
<220> FEATURE:
<221> NAME/KEY: MISC_FEATURE
<222> LOCATION: (76)..(76)
<223> OTHER INFORMATION: X= S or A
<220> FEATURE:
<221> NAME/KEY: MISC_FEATURE
<222> LOCATION: (77)..(77)
<223> OTHER INFORMATION: X= N, I or K
<220> FEATURE:
<221> NAME/KEY: MISC_FEATURE
<222> LOCATION: (78)..(78)
<223> OTHER INFORMATION: X= G, E or K
<220> FEATURE:
<221> NAME/KEY: MISC_FEATURE
<222> LOCATION: (79)..(79)
<223> OTHER INFORMATION: X= N, Y, D or T
<220> FEATURE:
<221> NAME/KEY: MISC_FEATURE
<222> LOCATION: (80)..(80)
<223> OTHER INFORMATION: X= V, K or I
<220> FEATURE:
<221> NAME/KEY: MISC_FEATURE
<222> LOCATION: (81)..(81)
<223> OTHER INFORMATION: X= T, A or I
<220> FEATURE:
<221> NAME/KEY: MISC_FEATURE
<222> LOCATION: (83)..(83)
<223> OTHER INFORMATION: X= S, L or T
<220> FEATURE:
<221> NAME/KEY: MISC_FEATURE
<222> LOCATION: (87)..(87)
<223> OTHER INFORMATION: X= E or V
<220> FEATURE:
<221> NAME/KEY: MISC_FEATURE
<222> LOCATION: (93)..(93)
<223> OTHER INFORMATION: X= E or K
<220> FEATURE:
<221> NAME/KEY: MISC_FEATURE
<222> LOCATION: (94)..(94)
<223> OTHER INFORMATION: X= K or R
<220> FEATURE:
<221> NAME/KEY: MISC_FEATURE
<222> LOCATION: (95)..(95)
<223> OTHER INFORMATION: X= N, T or S
<220> FEATURE:
<221> NAME/KEY: MISC_FEATURE
<222> LOCATION: (96)..(96)
<223> OTHER INFORMATION: X= I or F
<220> FEATURE:
<221> NAME/KEY: MISC_FEATURE
<222> LOCATION: (97)..(97)
<223> OTHER INFORMATION: X= K, N, A, or T
<220> FEATURE:
<221> NAME/KEY: MISC_FEATURE
<222> LOCATION: (101)..(101)
<223> OTHER INFORMATION: X= Q, K or E
<220> FEATURE:
<221> NAME/KEY: MISC_FEATURE
<222> LOCATION: (104)..(104)
<223> OTHER INFORMATION: X= V, I or K
<220> FEATURE:
<221> NAME/KEY: MISC_FEATURE
<222> LOCATION: (105)..(105)
<223> OTHER INFORMATION: X= H or R
<220> FEATURE:
<221> NAME/KEY: MISC_FEATURE
<222> LOCATION: (112)..(112)
<223> OTHER INFORMATION: X= N or Y
<220> FEATURE:
<221> NAME/KEY: MISC_FEATURE
<222> LOCATION: (113)..(113)
<223> OTHER INFORMATION: X= = T, S, P, L or A
```

```
<220> FEATURE:
<221> NAME/KEY: MISC_FEATURE
<222> LOCATION: (114)..(114)
<223> OTHER INFORMATION: X= = S or P

<400> SEQUENCE: 1

Xaa Trp Xaa Xaa Val Xaa Xaa Asp Leu Xaa Xaa Ile Xaa Xaa Leu Xaa
 1               5                  10                  15

Xaa Xaa Xaa His Xaa Asp Xaa Thr Leu Tyr Thr Xaa Ser Xaa Xaa His
            20                  25                  30

Pro Xaa Cys Lys Xaa Thr Xaa Met Xaa Cys Phe Leu Leu Glu Leu Xaa
        35                  40                  45

Val Ile Xaa Xaa Glu Xaa Xaa Xaa Xaa Xaa Xaa Xaa Xaa Xaa Xaa Xaa
 50                  55                  60

Asn Xaa Xaa Xaa Leu Ala Asn Xaa Xaa Leu Xaa Xaa Xaa Xaa Xaa Xaa
 65                  70                  75                  80

Xaa Glu Xaa Gly Cys Lys Xaa Cys Glu Glu Leu Glu Xaa Xaa Xaa Xaa
                85                  90                  95

Xaa Glu Phe Leu Xaa Ser Phe Xaa Xaa Ile Val Gln Met Phe Ile Xaa
            100                 105                 110

Xaa Xaa

<210> SEQ ID NO 2
<211> LENGTH: 114
<212> TYPE: PRT
<213> ORGANISM: Artificial Sequence
<220> FEATURE:
<223> OTHER INFORMATION: primate uinterleukin 15 consensus sequence
<220> FEATURE:
<221> NAME/KEY: MISC_FEATURE
<222> LOCATION: (1)..(1)
<223> OTHER INFORMATION: X = N or I
<220> FEATURE:
<221> NAME/KEY: MISC_FEATURE
<222> LOCATION: (4)..(4)
<223> OTHER INFORMATION: X = N or D
<220> FEATURE:
<221> NAME/KEY: MISC_FEATURE
<222> LOCATION: (10)..(10)
<223> OTHER INFORMATION: X = K or R
<220> FEATURE:
<221> NAME/KEY: MISC_FEATURE
<222> LOCATION: (11)..(11)
<223> OTHER INFORMATION: X = K or R
<220> FEATURE:
<221> NAME/KEY: MISC_FEATURE
<222> LOCATION: (13)..(13)
<223> OTHER INFORMATION: X = E or Q
<220> FEATURE:
<221> NAME/KEY: MISC_FEATURE
<222> LOCATION: (16)..(16)
<223> OTHER INFORMATION: X = I or T
<220> FEATURE:
<221> NAME/KEY: MISC_FEATURE
<222> LOCATION: (19)..(19)
<223> OTHER INFORMATION: X = M or I
<220> FEATURE:
<221> NAME/KEY: MISC_FEATURE
<222> LOCATION: (30)..(30)
<223> OTHER INFORMATION: X = D or G
<220> FEATURE:
<221> NAME/KEY: MISC_FEATURE
<222> LOCATION: (31)..(31)
<223> OTHER INFORMATION: X = V or I
<220> FEATURE:
<221> NAME/KEY: MISC_FEATURE
<222> LOCATION: (34)..(34)
<223> OTHER INFORMATION: X = S or R
<220> FEATURE:
<221> NAME/KEY: MISC_FEATURE
```

```
<222> LOCATION: (52)..(52)
<223> OTHER INFORMATION: X = L or H
<220> FEATURE:
<221> NAME/KEY: MISC_FEATURE
<222> LOCATION: (55)..(55)
<223> OTHER INFORMATION: X = G or N
<220> FEATURE:
<221> NAME/KEY: MISC_FEATURE
<222> LOCATION: (56)..(56)
<223> OTHER INFORMATION: X = D or N
<220> FEATURE:
<221> NAME/KEY: MISC_FEATURE
<222> LOCATION: (57)..(57)
<223> OTHER INFORMATION: X = A or T
<220> FEATURE:
<221> NAME/KEY: MISC_FEATURE
<222> LOCATION: (58)..(58)
<223> OTHER INFORMATION: X = S, N or D
<220> FEATURE:
<221> NAME/KEY: MISC_FEATURE
<222> LOCATION: (60)..(60)
<223> OTHER INFORMATION: X = H or N
<220> FEATURE:
<221> NAME/KEY: MISC_FEATURE
<222> LOCATION: (63)..(63)
<223> OTHER INFORMATION: X = V or I
<220> FEATURE:
<221> NAME/KEY: MISC_FEATURE
<222> LOCATION: (67)..(67)
<223> OTHER INFORMATION: X = I or L
<220> FEATURE:
<221> NAME/KEY: MISC_FEATURE
<222> LOCATION: (72)..(72)
<223> OTHER INFORMATION: X = N or R
<220> FEATURE:
<221> NAME/KEY: MISC_FEATURE
<222> LOCATION: (73)..(73)
<223> OTHER INFORMATION: X =S or I
<220> FEATURE:
<221> NAME/KEY: MISC_FEATURE
<222> LOCATION: (76)..(76)
<223> OTHER INFORMATION: X =S or A
<220> FEATURE:
<221> NAME/KEY: MISC_FEATURE
<222> LOCATION: (79)..(79)
<223> OTHER INFORMATION: X =N or T
<220> FEATURE:
<221> NAME/KEY: MISC_FEATURE
<222> LOCATION: (80)..(80)
<223> OTHER INFORMATION: X =V or I
<220> FEATURE:
<221> NAME/KEY: MISC_FEATURE
<222> LOCATION: (93)..(93)
<223> OTHER INFORMATION: X =E or K
<220> FEATURE:
<221> NAME/KEY: MISC_FEATURE
<222> LOCATION: (112)..(112)
<223> OTHER INFORMATION: X = N or Y
<220> FEATURE:
<221> NAME/KEY: MISC_FEATURE
<222> LOCATION: (113)..(113)
<223> OTHER INFORMATION: X = T or A

<400> SEQUENCE: 2

Xaa Trp Val Xaa Val Ile Ser Asp Leu Xaa Xaa Ile Xaa Asp Leu Xaa
1               5                   10                  15

Gln Ser Xaa His Ile Asp Ala Thr Leu Tyr Thr Glu Ser Xaa Xaa His
            20                  25                  30

Pro Xaa Cys Lys Val Thr Ala Met Lys Cys Phe Leu Leu Glu Leu Gln
        35                  40                  45

Val Ile Ser Xaa Glu Ser Xaa Xaa Xaa Ile Xaa Asp Thr Xaa Glu
    50                  55                  60

Asn Leu Xaa Ile Leu Ala Asn Xaa Xaa Leu Ser Xaa Asn Gly Xaa Xaa
65                  70                  75                  80
```

```
Thr Glu Ser Gly Cys Lys Glu Cys Glu Glu Leu Glu Xaa Lys Asn Ile
                85                  90                  95

Lys Glu Phe Leu Gln Ser Phe Val His Ile Val Gln Met Phe Ile Xaa
            100                 105                 110

Xaa Ser

<210> SEQ ID NO 3
<211> LENGTH: 114
<212> TYPE: PRT
<213> ORGANISM: Homo sapiens
<220> FEATURE:
<221> NAME/KEY: VARIANT
<222> LOCATION: (93)..(93)
<223> OTHER INFORMATION: X= E or K

<400> SEQUENCE: 3

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Ser Leu Glu Ser Gly Asp Ala Ser Ile His Asp Thr Val Glu
    50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Xaa Lys Asn Ile
                85                  90                  95

Lys Glu Phe Leu Gln Ser Phe Val His Ile Val Gln Met Phe Ile Asn
            100                 105                 110

Thr Ser

<210> SEQ ID NO 4
<211> LENGTH: 61
<212> TYPE: PRT
<213> ORGANISM: Artificial Sequence
<220> FEATURE:
<223> OTHER INFORMATION: mammalian sushi domain consensus sequence
<220> FEATURE:
<221> NAME/KEY: MISC_FEATURE
<222> LOCATION: (3)..(3)
<223> OTHER INFORMATION: X= P or A
<220> FEATURE:
<221> NAME/KEY: MISC_FEATURE
<222> LOCATION: (5)..(5)
<223> OTHER INFORMATION: X= M or V
<220> FEATURE:
<221> NAME/KEY: MISC_FEATURE
<222> LOCATION: (7)..(7)
<223> OTHER INFORMATION: X= V or I
<220> FEATURE:
<221> NAME/KEY: MISC_FEATURE
<222> LOCATION: (13)..(13)
<223> OTHER INFORMATION: X= W, R or Q
<220> FEATURE:
<221> NAME/KEY: MISC_FEATURE
<222> LOCATION: (16)..(16)
<223> OTHER INFORMATION: X= S or N
<220> FEATURE:
<221> NAME/KEY: MISC_FEATURE
<222> LOCATION: (19)..(19)
<223> OTHER INFORMATION: X= L or V
<220> FEATURE:
<221> NAME/KEY: MISC_FEATURE
<222> LOCATION: (20)..(20)
<223> OTHER INFORMATION: X= Y, H or N
```

```
<220> FEATURE:
<221> NAME/KEY: MISC_FEATURE
<222> LOCATION: (26)..(26)
<223> OTHER INFORMATION: X= I or V
<220> FEATURE:
<221> NAME/KEY: MISC_FEATURE
<222> LOCATION: (39)..(39)
<223> OTHER INFORMATION: X= S or T
<220> FEATURE:
<221> NAME/KEY: MISC_FEATURE
<222> LOCATION: (41)..(41)
<223> OTHER INFORMATION: X=T or I
<220> FEATURE:
<221> NAME/KEY: MISC_FEATURE
<222> LOCATION: (45)..(45)
<223> OTHER INFORMATION: X=T or I
<220> FEATURE:
<221> NAME/KEY: MISC_FEATURE
<222> LOCATION: (45)..(45)
<223> OTHER INFORMATION: X= L or I
<220> FEATURE:
<221> NAME/KEY: MISC_FEATURE
<222> LOCATION: (48)..(48)
<223> OTHER INFORMATION: X= A or N
<220> FEATURE:
<221> NAME/KEY: MISC_FEATURE
<222> LOCATION: (51)..(51)
<223> OTHER INFORMATION: X= V or A
<220> FEATURE:
<221> NAME/KEY: MISC_FEATURE
<222> LOCATION: (53)..(53)
<223> OTHER INFORMATION: X= H or Y

<400> SEQUENCE: 4

Cys Pro Xaa Pro Xaa Ser Xaa Glu His Ala Asp Ile Xaa Val Lys Xaa
1               5                   10                  15

Tyr Ser Xaa Xaa Ser Arg Glu Arg Tyr Xaa Cys Asn Ser Gly Phe Lys
            20                  25                  30

Arg Lys Ala Gly Thr Ser Xaa Leu Xaa Glu Cys Val Xaa Asn Lys Xaa
        35                  40                  45

Thr Asn Xaa Ala Xaa Trp Thr Thr Pro Ser Leu Lys Cys
    50                  55                  60

<210> SEQ ID NO 5
<211> LENGTH: 64
<212> TYPE: PRT
<213> ORGANISM: Artificial Sequence
<220> FEATURE:
<223> OTHER INFORMATION: enlarged mammalian sushi domain consensus
      sequence
<220> FEATURE:
<221> NAME/KEY: MISC_FEATURE
<222> LOCATION: (1)..(1)
<223> OTHER INFORMATION: X= T, V or I
<220> FEATURE:
<221> NAME/KEY: MISC_FEATURE
<222> LOCATION: (5)..(5)
<223> OTHER INFORMATION: X= P or A
<220> FEATURE:
<221> NAME/KEY: MISC_FEATURE
<222> LOCATION: (7)..(7)
<223> OTHER INFORMATION: X= M or V
<220> FEATURE:
<221> NAME/KEY: MISC_FEATURE
<222> LOCATION: (9)..(9)
<223> OTHER INFORMATION: X= V or I
<220> FEATURE:
<221> NAME/KEY: MISC_FEATURE
<222> LOCATION: (15)..(15)
<223> OTHER INFORMATION: X= W, R or Q
<220> FEATURE:
<221> NAME/KEY: MISC_FEATURE
<222> LOCATION: (18)..(18)
<223> OTHER INFORMATION: X= S or N
```

```
<220> FEATURE:
<221> NAME/KEY: MISC_FEATURE
<222> LOCATION: (21)..(21)
<223> OTHER INFORMATION: X=L or V
<220> FEATURE:
<221> NAME/KEY: MISC_FEATURE
<222> LOCATION: (22)..(22)
<223> OTHER INFORMATION: X=Y, H or N
<220> FEATURE:
<221> NAME/KEY: MISC_FEATURE
<222> LOCATION: (28)..(28)
<223> OTHER INFORMATION: X= I or V
<220> FEATURE:
<221> NAME/KEY: MISC_FEATURE
<222> LOCATION: (41)..(41)
<223> OTHER INFORMATION: X= S or T
<220> FEATURE:
<221> NAME/KEY: MISC_FEATURE
<222> LOCATION: (43)..(43)
<223> OTHER INFORMATION: X= T or I
<220> FEATURE:
<221> NAME/KEY: MISC_FEATURE
<222> LOCATION: (47)..(47)
<223> OTHER INFORMATION: X= L or I
<220> FEATURE:
<221> NAME/KEY: MISC_FEATURE
<222> LOCATION: (50)..(50)
<223> OTHER INFORMATION: X= A or N
<220> FEATURE:
<221> NAME/KEY: MISC_FEATURE
<222> LOCATION: (53)..(53)
<223> OTHER INFORMATION: X= V or A
<220> FEATURE:
<221> NAME/KEY: MISC_FEATURE
<222> LOCATION: (55)..(55)
<223> OTHER INFORMATION: X= H or Y

<400> SEQUENCE: 5

Xaa Thr Cys Pro Xaa Pro Xaa Ser Xaa Glu His Ala Asp Ile Xaa Val
1               5                   10                  15

Lys Xaa Tyr Ser Xaa Xaa Ser Arg Glu Arg Tyr Xaa Cys Asn Ser Gly
            20                  25                  30

Phe Lys Arg Lys Ala Gly Thr Ser Xaa Leu Xaa Glu Cys Val Xaa Asn
        35                  40                  45

Lys Xaa Thr Asn Xaa Ala Xaa Trp Thr Thr Pro Ser Leu Lys Cys Ile
    50                  55                  60

<210> SEQ ID NO 6
<211> LENGTH: 61
<212> TYPE: PRT
<213> ORGANISM: Artificial Sequence
<220> FEATURE:
<223> OTHER INFORMATION: primate sushi domain consensus sequence
<220> FEATURE:
<221> NAME/KEY: MISC_FEATURE
<222> LOCATION: (3)..(3)
<223> OTHER INFORMATION: X= P or A
<220> FEATURE:
<221> NAME/KEY: MISC_FEATURE
<222> LOCATION: (5)..(5)
<223> OTHER INFORMATION: X= M or V
<220> FEATURE:
<221> NAME/KEY: MISC_FEATURE
<222> LOCATION: (13)..(13)
<223> OTHER INFORMATION: X= W, R or Q
<220> FEATURE:
<221> NAME/KEY: MISC_FEATURE
<222> LOCATION: (20)..(20)
<223> OTHER INFORMATION: X= Y or H
<220> FEATURE:
<221> NAME/KEY: MISC_FEATURE
<222> LOCATION: (26)..(26)
<223> OTHER INFORMATION: X= I or V
<220> FEATURE:
```

```
<221> NAME/KEY: MISC_FEATURE
<222> LOCATION: (51)..(51)
<223> OTHER INFORMATION: X= V or A
<220> FEATURE:
<221> NAME/KEY: MISC_FEATURE
<222> LOCATION: (53)..(53)
<223> OTHER INFORMATION: X= V or A

<400> SEQUENCE: 6

Cys Pro Xaa Pro Xaa Ser Val Glu His Ala Asp Ile Xaa Val Lys Ser
1               5                   10                  15

Tyr Ser Leu Xaa Ser Arg Glu Arg Tyr Xaa Cys Asn Ser Gly Phe Lys
            20                  25                  30

Arg Lys Ala Gly Thr Ser Ser Leu Thr Glu Cys Val Leu Asn Lys Ala
        35                  40                  45

Thr Asn Xaa Ala Xaa Trp Thr Thr Pro Ser Leu Lys Cys
    50                  55                  60

<210> SEQ ID NO 7
<211> LENGTH: 63
<212> TYPE: PRT
<213> ORGANISM: Artificial Sequence
<220> FEATURE:
<223> OTHER INFORMATION: enlarged primate sushi domain consensus
      sequence
<220> FEATURE:
<221> NAME/KEY: MISC_FEATURE
<222> LOCATION: (1)..(1)
<223> OTHER INFORMATION: X= V or I
<220> FEATURE:
<221> NAME/KEY: MISC_FEATURE
<222> LOCATION: (5)..(5)
<223> OTHER INFORMATION: X= P or A
<220> FEATURE:
<221> NAME/KEY: MISC_FEATURE
<222> LOCATION: (7)..(7)
<223> OTHER INFORMATION: X= M or V
<220> FEATURE:
<221> NAME/KEY: MISC_FEATURE
<222> LOCATION: (15)..(15)
<223> OTHER INFORMATION: X= W, R or Q
<220> FEATURE:
<221> NAME/KEY: MISC_FEATURE
<222> LOCATION: (22)..(22)
<223> OTHER INFORMATION: X= Y or H
<220> FEATURE:
<221> NAME/KEY: MISC_FEATURE
<222> LOCATION: (28)..(28)
<223> OTHER INFORMATION: X= I or V
<220> FEATURE:
<221> NAME/KEY: MISC_FEATURE
<222> LOCATION: (53)..(53)
<223> OTHER INFORMATION: X=V or A
<220> FEATURE:
<221> NAME/KEY: MISC_FEATURE
<222> LOCATION: (55)..(55)
<223> OTHER INFORMATION: X=H or Y

<400> SEQUENCE: 7

Xaa Thr Cys Pro Xaa Pro Xaa Ser Val Glu His Ala Asp Ile Xaa Val
1               5                   10                  15

Lys Ser Tyr Ser Leu Xaa Ser Arg Glu Arg Tyr Xaa Cys Asn Ser Gly
            20                  25                  30

Phe Lys Arg Lys Ala Gly Thr Ser Ser Leu Thr Glu Cys Val Leu Asn
        35                  40                  45

Lys Ala Thr Asn Xaa Ala Xaa Trp Thr Thr Pro Ser Leu Lys Cys
    50                  55                  60

<210> SEQ ID NO 8
```

```
<211> LENGTH: 61
<212> TYPE: PRT
<213> ORGANISM: Homo sapiens

<400> SEQUENCE: 8

Cys Pro Pro Pro Met Ser Val Glu His Ala Asp Ile Trp Val Lys Ser
1               5                   10                  15

Tyr Ser Leu Tyr Ser Arg Glu Arg Tyr Ile Cys Asn Ser Gly Phe Lys
            20                  25                  30

Arg Lys Ala Gly Thr Ser Ser Leu Thr Glu Cys Val Leu Asn Lys Ala
        35                  40                  45

Thr Asn Val Ala His Trp Thr Thr Pro Ser Leu Lys Cys
50                  55                  60

<210> SEQ ID NO 9
<211> LENGTH: 64
<212> TYPE: PRT
<213> ORGANISM: Homo sapiens

<400> SEQUENCE: 9

Ile Thr Cys Pro Pro Pro Met Ser Val Glu His Ala Asp Ile Trp Val
1               5                   10                  15

Lys Ser Tyr Ser Leu Tyr Ser Arg Glu Arg Tyr Ile Cys Asn Ser Gly
            20                  25                  30

Phe Lys Arg Lys Ala Gly Thr Ser Ser Leu Thr Glu Cys Val Leu Asn
        35                  40                  45

Lys Ala Thr Asn Val Ala His Trp Thr Thr Pro Ser Leu Lys Cys Ile
50                  55                  60

<210> SEQ ID NO 10
<211> LENGTH: 77
<212> TYPE: PRT
<213> ORGANISM: Artificial Sequence
<220> FEATURE:
<223> OTHER INFORMATION: mammalian sushi and domains consensus sequence
<220> FEATURE:
<221> NAME/KEY: MISC_FEATURE
<222> LOCATION: (1)..(1)
<223> OTHER INFORMATION: X= T, V or I
<220> FEATURE:
<221> NAME/KEY: MISC_FEATURE
<222> LOCATION: (5)..(5)
<223> OTHER INFORMATION: X= P or A
<220> FEATURE:
<221> NAME/KEY: MISC_FEATURE
<222> LOCATION: (7)..(7)
<223> OTHER INFORMATION: X= M or V
<220> FEATURE:
<221> NAME/KEY: MISC_FEATURE
<222> LOCATION: (9)..(9)
<223> OTHER INFORMATION: X= V or I
<220> FEATURE:
<221> NAME/KEY: MISC_FEATURE
<222> LOCATION: (15)..(15)
<223> OTHER INFORMATION: X= W, R or Q
<220> FEATURE:
<221> NAME/KEY: MISC_FEATURE
<222> LOCATION: (18)..(18)
<223> OTHER INFORMATION: X= S or N
<220> FEATURE:
<221> NAME/KEY: MISC_FEATURE
<222> LOCATION: (21)..(21)
<223> OTHER INFORMATION: X= L or V
<220> FEATURE:
<221> NAME/KEY: MISC_FEATURE
<222> LOCATION: (22)..(22)
<223> OTHER INFORMATION: X= Y, H or N
<220> FEATURE:
<221> NAME/KEY: MISC_FEATURE
```

```
<222> LOCATION: (28)..(28)
<223> OTHER INFORMATION: X= I or V
<220> FEATURE:
<221> NAME/KEY: MISC_FEATURE
<222> LOCATION: (41)..(41)
<223> OTHER INFORMATION: X= S or T
<220> FEATURE:
<221> NAME/KEY: MISC_FEATURE
<222> LOCATION: (43)..(43)
<223> OTHER INFORMATION: X= T or I
<220> FEATURE:
<221> NAME/KEY: MISC_FEATURE
<222> LOCATION: (47)..(47)
<223> OTHER INFORMATION: X= L or I
<220> FEATURE:
<221> NAME/KEY: MISC_FEATURE
<222> LOCATION: (50)..(50)
<223> OTHER INFORMATION: X=A or N
<220> FEATURE:
<221> NAME/KEY: MISC_FEATURE
<222> LOCATION: (53)..(53)
<223> OTHER INFORMATION: X= V or A
<220> FEATURE:
<221> NAME/KEY: MISC_FEATURE
<222> LOCATION: (55)..(55)
<223> OTHER INFORMATION: X= H or Y
<220> FEATURE:
<221> NAME/KEY: MISC_FEATURE
<222> LOCATION: (55)..(55)
<223> OTHER INFORMATION: X= H or Y
<220> FEATURE:
<221> NAME/KEY: MISC_FEATURE
<222> LOCATION: (68)..(68)
<223> OTHER INFORMATION: X=A, S or L
<220> FEATURE:
<221> NAME/KEY: MISC_FEATURE
<222> LOCATION: (70)..(70)
<223> OTHER INFORMATION: X= V, A, S or T
<220> FEATURE:
<221> NAME/KEY: MISC_FEATURE
<222> LOCATION: (71)..(71)
<223> OTHER INFORMATION: X= H or R
<220> FEATURE:
<221> NAME/KEY: MISC_FEATURE
<222> LOCATION: (72)..(72)
<223> OTHER INFORMATION: X= Q or H
<220> FEATURE:
<221> NAME/KEY: MISC_FEATURE
<222> LOCATION: (73)..(73)
<223> OTHER INFORMATION: X= R, S or K
<220> FEATURE:
<221> NAME/KEY: MISC_FEATURE
<222> LOCATION: (75)..(75)
<223> OTHER INFORMATION: X= A, V or P
<220> FEATURE:
<221> NAME/KEY: MISC_FEATURE
<222> LOCATION: (76)..(76)
<223> OTHER INFORMATION: X= P or S
<220> FEATURE:
<221> NAME/KEY: MISC_FEATURE
<222> LOCATION: (77)..(77)
<223> OTHER INFORMATION: X= P or T

<400> SEQUENCE: 10

Xaa Thr Cys Pro Xaa Pro Xaa Ser Xaa Glu His Ala Asp Ile Xaa Val
 1               5                  10                  15

Lys Xaa Tyr Ser Xaa Xaa Ser Arg Glu Arg Tyr Xaa Cys Asn Ser Gly
            20                  25                  30

Phe Lys Arg Lys Ala Gly Thr Ser Xaa Leu Xaa Glu Cys Val Xaa Asn
        35                  40                  45

Lys Xaa Thr Asn Xaa Ala Xaa Trp Thr Thr Pro Ser Leu Lys Cys Ile
    50                  55                  60

Arg Asp Pro Xaa Leu Xaa Xaa Xaa Xaa Pro Xaa Xaa Xaa
65                  70                  75
```

```
<210> SEQ ID NO 11
<211> LENGTH: 77
<212> TYPE: PRT
<213> ORGANISM: Artificial Sequence
<220> FEATURE:
<223> OTHER INFORMATION: primate sushi and domains consensus sequence
<220> FEATURE:
<221> NAME/KEY: MISC_FEATURE
<222> LOCATION: (1)..(1)
<223> OTHER INFORMATION: X= V or I
<220> FEATURE:
<221> NAME/KEY: MISC_FEATURE
<222> LOCATION: (5)..(5)
<223> OTHER INFORMATION: X= P or A
<220> FEATURE:
<221> NAME/KEY: MISC_FEATURE
<222> LOCATION: (7)..(7)
<223> OTHER INFORMATION: X= M or V
<220> FEATURE:
<221> NAME/KEY: MISC_FEATURE
<222> LOCATION: (15)..(15)
<223> OTHER INFORMATION: X= W, R or Q
<220> FEATURE:
<221> NAME/KEY: MISC_FEATURE
<222> LOCATION: (22)..(22)
<223> OTHER INFORMATION: X= Y or H
<220> FEATURE:
<221> NAME/KEY: MISC_FEATURE
<222> LOCATION: (28)..(28)
<223> OTHER INFORMATION: X= I or V
<220> FEATURE:
<221> NAME/KEY: MISC_FEATURE
<222> LOCATION: (53)..(53)
<223> OTHER INFORMATION: X= V or A
<220> FEATURE:
<221> NAME/KEY: MISC_FEATURE
<222> LOCATION: (55)..(55)
<223> OTHER INFORMATION: X= H or Y
<220> FEATURE:
<221> NAME/KEY: MISC_FEATURE
<222> LOCATION: (68)..(68)
<223> OTHER INFORMATION: X= A, S or L
<220> FEATURE:
<221> NAME/KEY: MISC_FEATURE
<222> LOCATION: (70)..(70)
<223> OTHER INFORMATION: X= V, A or T
<220> FEATURE:
<221> NAME/KEY: MISC_FEATURE
<222> LOCATION: (71)..(71)
<223> OTHER INFORMATION: X= H or R
<220> FEATURE:
<221> NAME/KEY: MISC_FEATURE
<222> LOCATION: (75)..(75)
<223> OTHER INFORMATION: X= A or V

<400> SEQUENCE: 11

Xaa Thr Cys Pro Xaa Pro Xaa Ser Val Glu His Ala Asp Ile Xaa Val
1               5                   10                  15

Lys Ser Tyr Ser Leu Xaa Ser Arg Glu Arg Tyr Xaa Cys Asn Ser Gly
            20                  25                  30

Phe Lys Arg Lys Ala Gly Thr Ser Ser Leu Thr Glu Cys Val Leu Asn
        35                  40                  45

Lys Ala Thr Asn Xaa Ala Xaa Trp Thr Thr Pro Ser Leu Lys Cys Ile
    50                  55                  60

Arg Asp Pro Xaa Leu Xaa Xaa Gln Arg Pro Xaa Pro Pro
65                  70                  75

<210> SEQ ID NO 12
<211> LENGTH: 77
<212> TYPE: PRT
<213> ORGANISM: Homo sapiens
```

<400> SEQUENCE: 12

Ile Thr Cys Pro Pro Met Ser Val Glu His Ala Asp Ile Trp Val
1               5                   10                  15

Lys Ser Tyr Ser Leu Tyr Ser Arg Glu Arg Tyr Ile Cys Asn Ser Gly
                20                  25                  30

Phe Lys Arg Lys Ala Gly Thr Ser Ser Leu Thr Glu Cys Val Leu Asn
            35                  40                  45

Lys Ala Thr Asn Val Ala His Trp Thr Thr Pro Ser Leu Lys Cys Ile
        50                  55                  60

Arg Asp Pro Ala Leu Val His Gln Arg Pro Ala Pro Pro
65                  70                  75

<210> SEQ ID NO 13
<211> LENGTH: 20
<212> TYPE: PRT
<213> ORGANISM: Artificial Sequence
<220> FEATURE:
<223> OTHER INFORMATION: peptidic linker

<400> SEQUENCE: 13

Ser Gly Gly Ser Gly Gly Gly Gly Ser Gly Gly Gly Ser Gly Gly Gly
1               5                   10                  15

Gly Ser Leu Gln
            20

<210> SEQ ID NO 14
<211> LENGTH: 20
<212> TYPE: PRT
<213> ORGANISM: Artificial Sequence
<220> FEATURE:
<223> OTHER INFORMATION: peptidic linker

<400> SEQUENCE: 14

Ser Gly Gly Ser Gly Gly Gly Gly Ser Gly Gly Gly Ser Gly Gly Gly
1               5                   10                  15

Gly Ser Gly Gly
            20

<210> SEQ ID NO 15
<211> LENGTH: 21
<212> TYPE: PRT
<213> ORGANISM: Artificial Sequence
<220> FEATURE:
<223> OTHER INFORMATION: peptidic linker

<400> SEQUENCE: 15

Ser Gly Gly Gly Ser Gly Gly Gly Gly Ser Gly Gly Gly Gly Ser Gly
1               5                   10                  15

Gly Gly Ser Leu Gln
            20

<210> SEQ ID NO 16
<211> LENGTH: 22
<212> TYPE: PRT
<213> ORGANISM: Artificial Sequence
<220> FEATURE:
<223> OTHER INFORMATION: peptidic linker

<400> SEQUENCE: 16

Ser Gly Gly Gly Gly Ser Gly Gly Gly Gly Ser Gly Gly Gly Gly Ser
1               5                   10                  15

```
Gly Gly Gly Gly Ser Gly
            20

<210> SEQ ID NO 17
<211> LENGTH: 22
<212> TYPE: PRT
<213> ORGANISM: Artificial Sequence
<220> FEATURE:
<223> OTHER INFORMATION: peptidic linker

<400> SEQUENCE: 17

Ala Ala Gly Gly Gly Ser Gly Gly Ser Gly Gly Gly Ser Gly
1               5                   10                  15

Gly Gly Gly Ser Ala Ala
            20

<210> SEQ ID NO 18
<211> LENGTH: 211
<212> TYPE: PRT
<213> ORGANISM: Artificial Sequence
<220> FEATURE:
<223> OTHER INFORMATION: RLI1

<400> SEQUENCE: 18

Ile Thr Cys Pro Pro Pro Met Ser Val Glu His Ala Asp Ile Trp Val
1               5                   10                  15

Lys Ser Tyr Ser Leu Tyr Ser Arg Glu Arg Tyr Ile Cys Asn Ser Gly
            20                  25                  30

Phe Lys Arg Lys Ala Gly Thr Ser Ser Leu Thr Glu Cys Val Leu Asn
        35                  40                  45

Lys Ala Thr Asn Val Ala His Trp Thr Thr Pro Ser Leu Lys Cys Ile
    50                  55                  60

Arg Asp Pro Ala Leu Val His Gln Arg Pro Ala Pro Pro Ser Gly Gly
65                  70                  75                  80

Ser Gly Gly Gly Gly Ser Gly Gly Gly Ser Gly Gly Gly Gly Ser Leu
                85                  90                  95

Gln Asn Trp Val Asn Val Ile Ser Asp Leu Lys Lys Ile Glu Asp Leu
            100                 105                 110

Ile Gln Ser Met His Ile Asp Ala Thr Leu Tyr Thr Glu Ser Asp Val
        115                 120                 125

His Pro Ser Cys Lys Val Thr Ala Met Lys Cys Phe Leu Leu Glu Leu
    130                 135                 140

Gln Val Ile Ser Leu Glu Ser Gly Asp Ala Ser Ile His Asp Thr Val
145                 150                 155                 160

Glu Asn Leu Ile Ile Leu Ala Asn Asn Ser Leu Ser Ser Asn Gly Asn
                165                 170                 175

Val Thr Glu Ser Gly Cys Lys Glu Cys Glu Glu Leu Glu Glu Lys Asn
            180                 185                 190

Ile Lys Glu Phe Leu Gln Ser Phe Val His Ile Val Gln Met Phe Ile
        195                 200                 205

Asn Thr Ser
    210

<210> SEQ ID NO 19
<211> LENGTH: 211
<212> TYPE: PRT
<213> ORGANISM: Artificial Sequence
<220> FEATURE:
<223> OTHER INFORMATION: RLI2
```

```
<400> SEQUENCE: 19

Ile Thr Cys Pro Pro Met Ser Val Glu His Ala Asp Ile Trp Val
1               5                   10                  15

Lys Ser Tyr Ser Leu Tyr Ser Arg Glu Arg Tyr Ile Cys Asn Ser Gly
                20                  25                  30

Phe Lys Arg Lys Ala Gly Thr Ser Ser Leu Thr Glu Cys Val Leu Asn
            35                  40                  45

Lys Ala Thr Asn Val Ala His Trp Thr Thr Pro Ser Leu Lys Cys Ile
        50                  55                  60

Arg Asp Pro Ala Leu Val His Gln Arg Pro Ala Pro Pro Ser Gly Gly
65                  70                  75                  80

Ser Gly Gly Gly Gly Ser Gly Gly Gly Ser Gly Gly Gly Gly Ser Gly
                85                  90                  95

Gly Asn Trp Val Asn Val Ile Ser Asp Leu Lys Lys Ile Glu Asp Leu
                100                 105                 110

Ile Gln Ser Met His Ile Asp Ala Thr Leu Tyr Thr Glu Ser Asp Val
            115                 120                 125

His Pro Ser Cys Lys Val Thr Ala Met Lys Cys Phe Leu Leu Glu Leu
        130                 135                 140

Gln Val Ile Ser Leu Glu Ser Gly Asp Ala Ser Ile His Asp Thr Val
145                 150                 155                 160

Glu Asn Leu Ile Ile Leu Ala Asn Asn Ser Leu Ser Ser Asn Gly Asn
                165                 170                 175

Val Thr Glu Ser Gly Cys Lys Glu Cys Glu Glu Leu Glu Glu Lys Asn
            180                 185                 190

Ile Lys Glu Phe Leu Gln Ser Phe Val His Ile Val Gln Met Phe Ile
            195                 200                 205

Asn Thr Ser
        210
```

UNITED STATES PATENT AND TRADEMARK OFFICE
CERTIFICATE OF CORRECTION

| | |
|---|---|
| PATENT NO. | : 11,273,204 B2 |
| APPLICATION NO. | : 14/910475 |
| DATED | : March 15, 2022 |
| INVENTOR(S) | : Alain Gey, Eric Tartour and David Bechard |

It is certified that error appears in the above-identified patent and that said Letters Patent is hereby corrected as shown below:

In the Claims

Claim 1, Line 41, of Column 55 "1. An immunocytokine comprising of:" should be -- 1. An immunocytokine comprising --

Signed and Sealed this
Thirty-first Day of January, 2023

Katherine Kelly Vidal
*Director of the United States Patent and Trademark Office*